(12) United States Patent
Terada et al.

(10) Patent No.: US 11,414,382 B2
(45) Date of Patent: Aug. 16, 2022

(54) COMPOUND, PHOTOPOLYMERIZATION INITIATOR CONTAINING SAID COMPOUND, AND PHOTOSENSITIVE RESIN COMPOSITION CONTAINING SAID PHOTOPOLYMERIZATION INITIATOR

(71) Applicant: Nippon Kayaku Kabushiki Kaisha, Tokyo (JP)

(72) Inventors: Kiwamu Terada, Tokyo (JP); Hirokazu Kuwabara, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 170 days.

(21) Appl. No.: 16/976,798

(22) PCT Filed: Feb. 28, 2019

(86) PCT No.: PCT/JP2019/007775
§ 371 (c)(1),
(2) Date: Aug. 31, 2020

(87) PCT Pub. No.: WO2019/168089
PCT Pub. Date: Sep. 6, 2019

(65) Prior Publication Data
US 2021/0002216 A1 Jan. 7, 2021

(30) Foreign Application Priority Data
Mar. 2, 2018 (JP) .............................. JP2018-037131

(51) Int. Cl.
*C07C 323/22* (2006.01)
*C07D 213/75* (2006.01)
(Continued)

(52) U.S. Cl.
CPC .......... *C07C 323/22* (2013.01); *C07D 213/75* (2013.01); *C07D 213/85* (2013.01);
(Continued)

(58) Field of Classification Search
CPC .......................... C07D 213/75; C07D 213/85; C07D 295/205; C07C 271/66; C07C 271/10;
(Continued)

(56) References Cited

U.S. PATENT DOCUMENTS 6,057,380 A 5/2000 Birbaum et al.
6,124,371 A 9/2000 Stanssens et al.
(Continued)

FOREIGN PATENT DOCUMENTS

JP 2000330270 A 11/2000
JP 3250072 B2 1/2002
(Continued)

OTHER PUBLICATIONS

English translation of JP2008250111. (Year: 2008).*
(Continued)

*Primary Examiner* — Chanceity N Robinson
*Assistant Examiner* — Anna Malloy
(74) *Attorney, Agent, or Firm* — The Webb Law Firm

(57) ABSTRACT

This compound, which absorbs long-wavelength active energy rays and generates with high-efficiency radicals and strong bases, and which has excellent reaction efficiency in a base generating chain reaction, is represented by formula (1), where, in formula (1), $R_1$, $R_2$, $R_3$, $R_5$ and $R_6$ independently represent a hydroxy group, an alkoxy group, or an organic group other than those substituents, the $R_4$'s independently represent an organic group including a thioether bond, and 'A' represents a substituent represented by formula (1-1) or (1-2), where, in formula (1-1), $R_7$ and $R_8$ independently represent a hydrogen atom, an alkyl group or a heterocyclic group, and where, in formula (1-2), $R_9$ and $R_{10}$ independently represent an amino group or a substituted amino group. A photopolymerization initiator can include said compound; and a photosensitive resin composition can include said photopolymerization initiator.

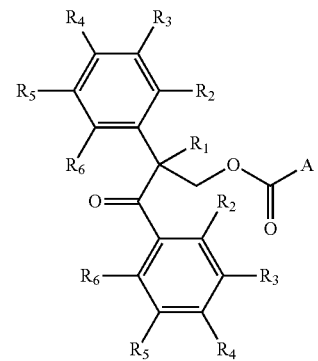

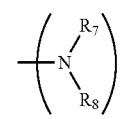

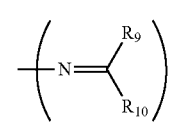

9 Claims, No Drawings

(51) Int. Cl.
  *C07D 213/85* (2006.01)
  *C07D 295/205* (2006.01)
  *C08F 2/50* (2006.01)
  *G03F 7/031* (2006.01)

(52) U.S. Cl.
  CPC ............ *C07D 295/205* (2013.01); *C08F 2/50* (2013.01); *G03F 7/031* (2013.01)

(58) Field of Classification Search
  CPC ... C07C 271/24; C07C 271/26; C07C 271/28; C07C 323/62; C07C 323/31; G03F 7/031
  See application file for complete search history.

(56) References Cited

U.S. PATENT DOCUMENTS

| | | | |
|---|---|---|---|
| 7,253,131 B2 * | 8/2007 | Watanabe | ............... C09K 3/10 502/159 |
| 7,300,747 B2 | 11/2007 | Okazaki et al. | |
| 7,759,043 B2 | 7/2010 | Tanabe et al. | |
| 10,508,078 B2 * | 12/2019 | Terada | ................ C07C 271/24 |
| 2010/0210749 A1 | 8/2010 | Taguchi | |

FOREIGN PATENT DOCUMENTS

| | | | | |
|---|---|---|---|---|
| JP | 2004359639 | A | | 12/2004 |
| JP | 200597141 | A | | 4/2005 |
| JP | 2005220097 | A | | 8/2005 |
| JP | 2005264156 | A | | 9/2005 |
| JP | 2006160634 | A | | 6/2006 |
| JP | 2007101685 | A | | 4/2007 |
| JP | 200894770 | A | | 4/2008 |
| JP | 2008509967 | A | | 4/2008 |
| JP | 2008250111 | A | | 10/2008 |
| JP | 2008250111 | A | * | 10/2008 |
| JP | 200940762 | A | | 2/2009 |
| JP | 4344400 | B1 | | 10/2009 |
| JP | 201180036 | A | | 4/2011 |
| JP | 2011190241 | A | | 9/2011 |
| JP | 2012180310 | A | | 9/2012 |
| JP | 5561693 | B2 | | 7/2014 |
| JP | 5725515 | B2 | | 5/2015 |
| JP | 2017105749 | A | | 6/2017 |
| JP | 201952268 | A | | 4/2019 |
| JP | 201966779 | A | | 4/2019 |
| KR | 1020060053095 | A | | 5/2006 |
| KR | 1020130066483 | A | | 6/2013 |
| WO | 9731033 | A1 | | 8/1997 |
| WO | WO-2017099130 | A1 | * | 6/2017 ........... C07C 269/02 |
| WO | 2017141723 | A1 | | 8/2017 |
| WO | 2018207836 | A1 | | 11/2018 |
| WO | 2019168113 | A1 | | 9/2019 |

OTHER PUBLICATIONS

Ishikawa et al., "Photosensitivity Characteristics of UV Curable Organic-Inorganic Hybrids Sensitized with Benzoin Derivatives as Photobase Generators", Journal of Photopolymer Science and Technology, 2014, pp. 223-225, vol. 27:2.

Ishikawa et al., "Development of Photobase Generator with Benzoin Derivatives and its Application to Photosensitive Materials", Chemistry Letters, 2014, pp. 612-614, vol. 43:5.

Terada et al., "Polymer Preprints, Japan", The Society of Polymer Science, Japan, 2017, pp. 1-4, vol. 66:1.

Terada et al., "Polymer Preprints, Japan", The Society of Polymer Science, 2017, pp. 1-4, vol. 66:2.

Zhang et al., "Visible-Light-Initiated Thiol-Michael Addition Polymerizations with Coumarin-Based Photobase Generators: Another Photoclick Reaction Strategy", ACS Macro Letters, 2016, pp. 229-233.

Arimitsu et al., "Synthesis of a Novel Photobase Generator Having a Base-Proliferating Group and its Application to a Negative-Type Photopolymer", The Society of Polymer Science, Japan, 2014, pp. 53-58, vol. 71:2.

Shikawa et al., "Photosensitivity Characteristics of UV Curable Organic-Inorganic Hybrids Sensitized with Benzoin Derivatives as Photobase Generators", Journal of Photopolymer Science and Technology, 2014, pp. 223-225, vol. 27:2.

Shikawa et al., "Development of Photobase Generator with Benzoin Derivatives and its Application to Photosensitive Materials", Chemistry Letters, 2014, pp. 612-614, vol. 43:5.

* cited by examiner

COMPOUND, PHOTOPOLYMERIZATION INITIATOR CONTAINING SAID COMPOUND, AND PHOTOSENSITIVE RESIN COMPOSITION CONTAINING SAID PHOTOPOLYMERIZATION INITIATOR

CROSS-REFERENCE TO RELATED APPLICATIONS

This application is the United States national phase of International Application No. PCT/JP2019/007775 filed Feb. 28, 2019, and claims priority to Japanese Patent Application No. 2018-037131 filed Mar. 2, 2018, the disclosures of which are hereby incorporated by reference in their entirety.

BACKGROUND OF THE INVENTION

Technical Field

The present invention relates to a novel compound, a photopolymerization initiator containing the compound which generates a base and a radical by irradiation of active energy ray, and a photosensitive resin composition containing the photopolymerization initiator.

Background Art

A photoacid generator generating a strong acid by irradiation of active energy ray such as light, infrared rays, electron beam or X-ray, and a chemical amplification resist where the photoacid generator is formulated into a resin component have been conventionally known and are used for several applications.

In such chemical amplification resist, the strong acid generated by the irradiation of the active energy ray acts as a catalyst to the resin component so as to change the solubility of the resin to the developing solution to form a pattern. For high sensitivity and high resolution, various resist materials have been developed, however the combinations of the photoacid generators with the resins are limited. Therefore, the development of new chemical amplification resist is demanded.

The UV curing technology of a monomer and a prepolymer by the irradiation of active energy ray is classified roughly to three types of a radical type, a cationic type and an anionic type. Among them, the technique that vinyl monomers are polymerized by irradiation to photoradical polymerization initiator is the most widely developed. In addition, the technique that an acid generated by the action of light is used as cation to conduct cationic polymerization is also studied.

However, in the radical polymerization, because the polymerization is interrupted by the oxygen in the air, specific ingenuity is needed for blocking the oxygen. In the cationic polymerization, the block of the oxygen is not needed, which is more advantageous. However, the possible corrosivity and the resin modification caused by the strong acid generated from the photoacid generator remaining after curing are pointed out. Therefore, it is strongly demanded that a photosensitive resin composition containing no corrosive substance such as strong acid, being not inhibited by the oxygen in the air, and providing quick reaction progress in high efficiency is developed.

As a method for overcoming the above problems, it is studied that a photosensitive resin composition is used for a photoresist and a photocurable material etc., by using polymerization reactions and chemical reactions under a base catalyst, for example where a resin is chemically modified due to a base generated by light action as a catalyst. More specifically, proposed is a method that amines capable of working as an initiator or a catalyst by the action of light or heat are generated in an epoxy resin layer, and then curing by heat treatment is conducted, which utilizing the feature that a resin (compound) having epoxy groups is cross-linked and cured by the action of base.

For example, Patent Literature 1 to 4 describe the photobase generators generating organic strong bases. However, the molecules of the photobase generators described in the Patent Literature 1 to 4 are ionic, therefore, the photobase generators have low solubility in an organic solvent used generally in the industry and also have low storage stability when mixed with a resin. Accordingly, the improvement is required.

Patent Literature 5 describes the photosensitive resin composition using α-aminoketone compound as a latent base catalyst.

However, the α-aminoketone compound described in Patent Literature 5 is not practical, because the α-aminoketone compound generates a small amount of base and cannot accelerate the base catalytic reaction sufficiently.

Patent Literature 6 discloses the photobase generator absorbing active energy ray in a long wavelength region and generating a base and a radical in higher efficiency.

However, the base generated by the photobase generator described in Patent Literature 6 is an aliphatic primary amine and does not have sufficient base strength for proceeding with the base catalytic reaction efficiently.

Non-Patent Literature 1 describes a photobase generator generating an aliphatic secondly amine by irradiation of active energy ray. The photobase generator of Non-Patent Literature 1 has a low photosensitivity and is not practical, because the wavelength of absorbed light is short and the light in a long wavelength region cannot be absorbed.

CITATION LIST

Patent Literature

Patent Literature 1: JP 2005-264156 A
Patent Literature 2: JP 2007-101685 A
Patent Literature 3: JP 5,725,515 B
Patent Literature 4: JP 5,561,693 B
Patent Literature 5: JP 3,250,072 B
Patent Literature 6: JP 2017-105749 A

Non-Patent Literature

Non-Patent literature 1: Chem. Lett., 2014, 43, 612-614
Non-Patent literature 2: Koji Arimitsu et al. KOBUNSHI RONBUNSHU (Japanese Journal of Polymer Science and Technology) Vol. 71, No. 2 (2014), p53-58 (Feb. 25, 2014)

SUMMARY OF INVENTION

Technical Problem

In view of the above problems, the objects of present invention are to provide a new compound capable of highly efficiently producing a radical and a base having high strength by absorbing long wavelength active energy ray and being excellent in the base catalyst reaction efficiency after the production of the base for example, in the case of using for the cross-linking reaction of siloxane compound, a photopolymerization initiator containing the new compound and a photosensitive resin composition containing the photopolymerization initiator.

Solution to Problem

By the earnest research, the present inventors found to solve the problems by using a compound having a specific structure as a photopolymerization initiator so as to finish the present invention.

That is, the present invention relates to:

[1] A compound having a following chemical formula (1):

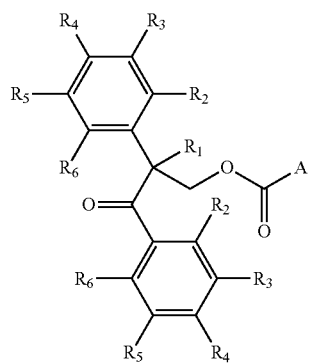

wherein in formula (1), $R_1$ represents a hydroxy group, an alkoxy group or an organic group other than the aforementioned substituents; $R_2$, $R_3$, $R_5$ and $R_6$ each independently represent hydrogen atom, halogen atom, hydroxy group, alkoxy group, mercapto group, sulfide group, silyl group, silanol group, nitro group, nitroso group, cyano group, sulfino group, sulfo group, sulfonato group, phosphino group, phosphinyl group, phosphono group, phosphonato group, amino group, ammonio group or an organic group other than the aforementioned substituents, each of $R_2$, $R_3$, $R_5$ and $R_6$ plurally existing may be the same or different from each other; $R_2$ and $R_3$ on the same benzene ring may be connected to form a ring structure and $R_5$ and $R_6$ on the same benzene ring may be connected to form a ring structure; $R_4$ each independently represents a hydrogen atom or an organic group having a thioether bond, and at least one of $R_4$ is the organic group having a thioether bond; the organic group having a thioether bond represented by $R_4$ and $R_3$ or $R_5$ may be connected to form a ring structure; A is a substituent having a formula (1-1) or (1-2):

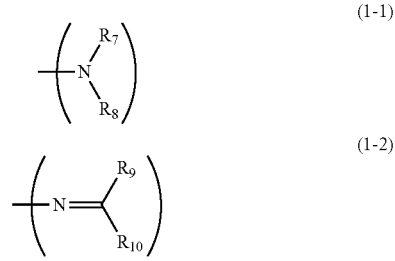

wherein in formula (1-1), $R_7$ and $R_8$ each independently represent a hydrogen atom or an alkyl group or a hetero cyclic group, or $R_7$ and $R_8$ may be connected to form a cyclic group; in formula (1-2), $R_9$ and $R_{10}$ each independently represent an amino group or a substituted amino group.

[2] The compound according to [1], wherein one of $R_4$ is the alkyl group having a thioether bond or the aryl group having a thioether bond, and the other is the hydrogen atom, the alkyl group having a thioether bond or the aryl group having a thioether bond.

[3] The compound according to [1] or [2], wherein $R_1$ is the hydroxy group.

[4] A photopolymerization initiator containing the compound according to any one of [1] to [3].

[5] A photosensitive resin composition containing the photopolymerization initiator according to [4] and a polymer precursor capable of being polymerized by irradiation or by both of irradiation and heating in presence of a photopolymerization initiator.

[6] The photosensitive resin composition according to [5], wherein the polymer precursor comprises at least one selected from the group consisting of a compound having a substituent selected from the group consisting of an epoxy group, an isocyanate group, an oxetane group, an acryloyl group, a methacryloyl group, a maleimide group and a thiirane group; a polysiloxane precursor; a polyimide precursor; and a polybenzoxazole precursor.

[7] The photosensitive resin composition according to [6], wherein the polymer precursor comprises the compound having an epoxy group.

[8] The photosensitive resin composition according to [6], wherein the polymer precursor comprises the compound having an acryloyl group and the polysiloxane precursor.

[9] A cured product obtained by curing the photosensitive resin composition according to any one of [5] to [8].

Effects of the Invention

The compound represented by formula (1) of the present invention is able to produce a base and a radical by the irradiation of the active energy ray. Furthermore, because the produced base is the amine having high base strength or working as base catalyst, which has high quantum yield of cleavage, the compound can be used as a photopolymerization initiator having the sensitivity superior to a conventional photobase generator. Furthermore, the photosensitive resin composition containing the compound produces no acid providing metal corrosion by the irradiation of the active energy ray, therefore, the composition can be suitably used for metal materials.

DESCRIPTION OF THE INVENTION

The present invention is described below in detail.

Note that the active energy ray in the present invention includes particle rays such as electron rays, and radical rays or ionization radiation which are generic terms of electromagnetic waves and particle rays in addition to visible light, provided that the case where a wavelength is specified is excluded. In this specification, the irradiation of the active energy ray may be referred to as exposure. Also, note that the active energy ray of a wavelength of 365 nm, 405 nm and 436 nm may be transcribed into f-ray, h-ray, and g-ray, respectively.

The compound of the present invention is represented by formula (1).

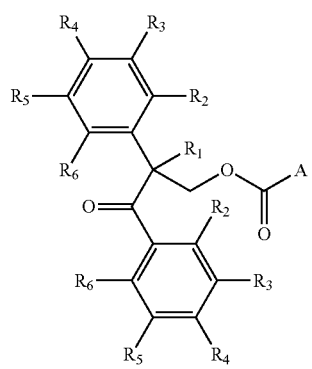

(1)

In formula (1), $R_1$ represents, a hydroxy group, an alkoxy group or an organic group other than the aforementioned substituents.

The alkoxy group represented by $R_1$ in formula (1) is preferably an alkoxy group having a carbon number of 1 to 18. Examples of the alkoxy group include methoxy group, ethoxy group, n-propoxy group, iso-propoxy group, n-butoxy group, iso-butoxy group, sec-butoxy group, t-butoxy group, n-pentoxy group, iso-pentoxy group, neo-pentoxy group, n-hexyloxy group and n-dodecyloxy group.

Examples of the organic group represented by $R_1$ of formula (1) include an alkyl group having a carbon number of 1 to 18, an alkenyl group having a carbon number of 2 to 18, an alkynyl group having a carbon number of 2 to 18, an aryl group having a carbon number of 6 to 12, an acyl group having a carbon number 1 to 18, an aroyl group having a carbon number of 7 to 18, a nitro group, a cyano group, an alkylthio group having a carbon number of 1 to 18 and halogen atom.

Examples of the alkyl group having a carbon number of 1 to 18 described as the organic group represented by $R_1$ of formula (1) include a straight or branched alkyl group such as methyl group, ethyl group, n-propyl group, isopropyl group, n-butyl group, iso-butyl group, sec-butyl, t-butyl, n-pentyl group, n-hexyl group, n-heptyl group, n-octyl group, n-nonyl group, n-decyl, n-undecyl group and n-dodecyl group, and a cyclic alkyl group such as cyclopropyl group, cyclobutyl group, cyclopentyl group and cyclohexyl group. The alkyl group is preferably an alkyl group having a carbon number of 2 to 6, more preferably a linear or branched alkyl group having a carbon number of 2 to 6.

Examples of the alkenyl groups having a carbon number of 2 to 18 described as the organic group represented by $R_1$ of formula (1) include vinyl group, propenyl group, 1-butenyl group, iso-butenyl group, 1-pentenyl group, 2-pentenyl group, 2-methyl-1-butenyl group, 3-methyl-1-butenyl group, 2-methyl-2-butenyl group, 2,2-dicyanovinyl group, 2-cyano-2-methylcarboxyvinyl group and 2-cyano-2-methylsulfonevinyl group.

Examples of the alkynyl group having a carbon number of 2 to 18 described as the organic group represented by $R_1$ of formula (1) include ethynyl group, 1-propynyl group and 1-butynyl group.

Examples of the aryl groups having a carbon number of 6 to 12 described as the organic group represented by $R_1$ of formula (1) include phenyl group, naphthyl group and tolyl group. The aryl group is preferably an aryl group having a carbon number of 6 to 10.

Examples of the acyl groups having a carbon number of 1 to 18 described as the organic group represented by $R_1$ of formula (1) include formyl group, acetyl group, ethylcarbonyl group, n-propylcarbonyl group, iso-propylcarbonyl group, n-butylcarbonyl group, n-pentylcarbonyl group, iso-pentylcarbonyl group, neo-pentylcarbonyl group, 2-methylbutyl carbonyl group and nitrobenzylcarbonyl group.

Examples of the aroyl groups having a carbon number of 7 to 18 described as the organic group represented by $R_1$ of formula (1) include benzoyl group, toluoyl group, naphthoyl group and phthaloyl group.

Examples of the alkylthio group having a carbon number of 1 to 18 described as the organic group represented by $R_1$ of formula (1) include methylthio group, ethylthio group, n-propylthio group, iso-propylthio group, n-butylthio group, iso-butylthio group, sec-butylthio group, t-butylthio group, n-pentylthio group, iso-pentylthio group, 2-methylbutylthio group, 1-methylbutylthio group, neo-pentylthio group, 1,2-dimethylpropylthio group and 1,1-dimethylpropylthio group.

Examples of the halogen atom described of the organic group represented by $R_1$ of formula (1) include fluorine atom, chlorine atom, bromine atom and iodine atom.

$R_1$ in formula (1) is preferably a hydroxy group or an alkoxy group, more preferably a hydroxy group or an alkoxy group having a carbon number of 1 to 6, further preferably a hydroxy group or an alkoxy group having a carbon number of 1 to 4, especially preferably a hydroxy group.

In formula (1), $R_2$, $R_3$, $R_5$ and $R_6$ each independently represent hydrogen atom, halogen atom, hydroxy group, alkoxy group, mercapto group, sulfide group, silyl group, silanol group, nitro group, nitroso group, cyano group, sulfino group, sulfo group, sulfonate group, phosphino group, phosphinyl group, phosphono group, phosphonato group, amino group, ammonio group or organic group other than the aforementioned groups. Each of $R_2$, $R_3$, $R_5$ and $R_6$ plurally existing may be the same or different from each other. $R_2$ and $R_3$ existing on the same benzene ring may be connected to form a ring structure, $R_5$ and $R_6$ existing on the same benzene ring may be connected to form a ring structure, and the ring structure may have a bond with a hetero atom.

Examples of the halogen atom represented by $R_2$, $R_3$, $R_5$ and $R_6$ of formula (1) include the same one as the examples described in the halogen atoms represented by $R_1$ in formula (1).

Examples of the alkoxy group represented by $R_2$, $R_3$, $R_5$ and $R_6$ of formula (1) include the same one as the examples described in the alkoxy group represented by $R_1$ in formula (1).

Examples of the organic group represented by $R_2$, $R_3$, $R_5$ and $R_6$ of formula (1) include alkyl group, aryl group, aralkyl group, halogenated alkyl group, isocyano group, cyanate group, isocyanato group, thiocyanato group, isothiocyanato group, alkoxycarbonyl group, carbamoyl group, thiocarbamoyl group, carboxyl group, carboxylate group, acyl group, acyloxy group, and hydroxyimino group.

Examples of the alkyl group, the aryl group and the acyl group as examples of the organic group represented by $R_2$, $R_3$, $R_5$ and $R_6$ of formula (1) include the same one as the examples described in the alkyl group, the aryl group and the acyl group as examples of the organic group represented by $R_1$ in formula (1).

These organic groups may have a bond with a hetero atom except for a hydrocarbon in the organic group, and may have a substituent except for hydrocarbon group, which may be linear or branched. The organic group of $R_2$, $R_3$, $R_5$ and $R_6$ is usually a monovalent organic group, but, in the case where a ring structure is formed described below, the organic group may be a di- or more valent organic group.

A bond except for the bond of a hydrocarbon group which may be included in the organic group represented by $R_2$, $R_3$, $R_5$ and $R_6$ is not particularly limited as far as the advantageous effects are not damaged. Examples of the bond except for the bond of the hydrocarbon include an ether bond, a thioether bond, a carbonyl bond, a thiocarbonyl bond, an ester bond, an amide bond, a urethane bond, a carbonate bond, a sulfonyl bond, a sulfinyl bond, an azo bond. As a bond in the organic group except for the bond of the hydrocarbon group, an ether bond, a thioether bond, a carbonyl bond, a thiocarbonyl bond, an ester bond, an amide bond, a urethane bond, an imino bond (—N=C(—R)—, —C(=NR)— wherein R represents a hydrogen atom or an organic group), a carbonate bond, a sulfonyl bond and a sulfinyl bond are preferable, in view of the heat resistant.

A substituent except for a hydrocarbon group which the organic group represented by $R_2$, $R_3$, $R_5$ and $R_6$ can have is not particularly limited as far as the advantageous effects are not damaged. Examples of the substituent except for the hydrocarbon group includes halogen atom, hydroxy group, mercapto group, sulfide group, cyano group, isocyano group, cyanate group, isocyanato group, thiocyanato group, isothiocyanato group, silyl group, silanol group, alkoxy group, alkoxycarbonyl group, carbamoyl group, thiocarbamoyl group, nitro group, nitroso group, carboxyl group, carboxylate group, acyl group, acyloxy group, sulfino group, sulfo group, sulfonato group, phosphino group, phosphinyl group, phosphono group, phosphonato group, hydroxy imino group, saturated or unsaturated alkyl ether group, saturated or unsaturated alkylthio ether group, aryl ether group, arylthio ether group, amino group (—NH$_2$, —NHR, and —NRR': wherein R and R' are independently hydrocarbon group), and ammonio group. The hydrogen included in the above substituents may be substituted for a hydrocarbon group. The hydrocarbon group included in the substituents may be linear, branched or cyclic. Among them, the preferable substituents except for the hydrocarbon group in the organic group of $R_2$, $R_3$, $R_5$ and $R_6$ are halogen atom, hydroxy group, mercapto group, sulfide group, cyano group, isocyano group, cyanato group, isoxyanato group, thiocyanato group, isothiocyanato group, silyl group, silanol group, alkoxy group, alkoxycarbonyl group, carbamoyl group, thiocarbamoyl group, nitro group, nitroso group, carboxyl group, carboxylate group, acyl group, acyloxy group, sulfino group, sulfo group, sulfonato group, phosphino group, phosphinyl group, phosphono group, phosphonato group, hydroxyimino group, saturated or unsaturated alkyl ether group, saturated or unsaturated alkylthioether group, arylether group and arylthioether group.

$R_2$ and $R_3$ existing on the same benzene ring may be connected to form a cyclic structure, and $R_5$ and $R_6$ existing on the same benzene ring may be connected to form a cyclic structure. The cyclic structure may be a saturated or unsaturated alicyclic hydrocarbon, a heterocyclic hydrocarbon, a condensed ring hydrocarbon and a structure having the combination of two or more selected from the saturated or unsaturated alicyclic hydrocarbon, the heterocyclic hydrocarbon and the condensed ring hydrocarbon. For example, $R_2$ and $R_3$ are connected and/or $R_5$ and $R_6$ are connected to each other to share the atoms of the benzene ring connected to $R_2$, $R_3$, $R_5$ and $R_6$ so as to form a condensed ring such as a naphthalene, an anthracene, a phenanthrene and an indene.

The preferred examples of the organic group represented by $R_2$, $R_3$, $R_5$ and $R_6$ include alkyl group having a carbon number of carbon 1 to 20 such as methyl group, ethyl group and propyl group; a cycloalkyl group having a carbon number of 4 to 23 such as cyclopentyl group and cyclohexyl group; cycloalkenyl group having a carbon number of 4 to 23 such as cyclopentenyl group and cyclohexenyl group; an aryloxy alkyl group (—ROAr group) having a carbon number of 7 to 26 such as phenoxymethyl group, 2-phenoxyethyl group and 4-phenoxybutyl group; aralkyl group having a carbon number of 7 to 20 such as benzyl group and 3-phenylpropyl group; alkyl group having a cyano group having a carbon number of 2 to 21 such as cyanomethyl group and β-cyanoethyl group; alkyl group having a hydroxy group having a carbon number of 1 to 20 such as hydroxymethyl group; alkoxy group having a carbon number of 1 to 20 such as methoxy group and ethoxy group; amido group having a carbon number of 2 to 21 such as acetamide group and benzenesulfonamide group (C$_6$H$_5$SO$_2$NH—); alkylthio group (—SR group) having a carbon number of 1 to 20 such as methylthio group and ethylthio group; acyl group having a carbon number of 1 to 20 such as acetyl group and benzoyl group; ester group (—COOR group and —OCOR group) having a carbon number of 2 to 21 such as methoxy carbonyl group and acetoxy group; aryl group having a carbon number of 6 to 20 such as phenyl group, naphthyl group, biphenyl group and tolyl group; aryl group having a carbon number of 6 to 20 where an electron-donating group and/or an electron-withdrawing group is/are substituted; benzyl group where an electron-donating group and/or an electron-withdrawing group is/are substituted; cyano group; and methylthio group (—SCH$_3$ group). The alkyl moiety of the substituent described above may be linear, branched or cyclic.

Also, when in the compound at least one of $R_2$, $R_3$, $R_5$ and $R_6$ is a hydroxy group, the solubility in a basic aqueous solution, etc., can be improved and also the absorption wavelength of the compound represented by formula (1) can become longer, compared with a case where none of $R_2$, $R_3$, $R_5$ and $R_6$ is a hydroxy group.

It is preferable that all $R_2$, $R_3$, $R_5$ and $R_6$ in formula (1) are hydrogen atoms.

In formula (1), $R_4$ each independently represents a hydrogen atom or an organic group having a thioether bond. At least one of $R_4$ is an organic group having a thioether bond. The organic group having a thioether bond represented by $R_4$ may be connected to $R_3$ or $R_5$ to form a ring structure.

Examples of the organic group mentioned in the above include the same organic group represented by $R_2$, $R_3$, $R_5$ and $R_6$ in formula (1), but the organic group represented by $R_4$ is preferably alkyl group or aryl group. Therefore, $R_4$ in formula (1) is preferably alkylthio group or arylthio group, more preferably alkylthio group having a carbon number of 1 to 20. In this specification, as an example of the organic group having a thioether bond, the alkyl group (the aryl group) having a thioether bond include the embodiment "—S-Alkyl group (Aryl group)". In this case, the sulfur atom of the thioether bond is directly connected to the benzene ring which the structure formula (1) has.

The ring structure formed by connecting the organic group having a thioether bond represented by $R_4$ to $R_3$ or $R_5$ may be saturated or unsaturated alicyclic hydrocarbon, heterocyclic hydrocarbon, condensed ring hydrocarbon and structure having the combination of two or more selected from the saturated or unsaturated alicyclic hydrocarbon, the heterocyclic hydrocarbon and the condensed ring hydrocarbon.

In formula (1), A represents the substituent group represented by formula (1-1) or formula (1-2).

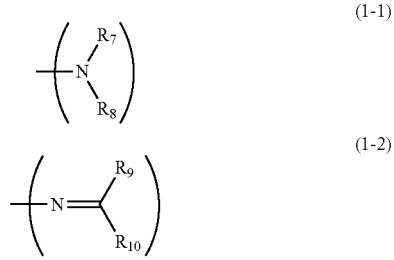

In formula (1-1), $R_7$ and $R_8$ each independently represent a hydrogen atom, an alkyl group, or a heterocyclic group or may be connected to form a heterocyclic ring.

Examples of the alkyl group represented by $R_7$ and $R_8$ of formula (1-1) include an alkyl group having a carbon number of 1 to 18 as an example of the organic group represented by $R_1$ in formula (1), and the alkyl group as a substituent which the heterocyclic group represented by $R_7$ and $R_8$ of formula (1-1) described below has.

Examples of the heterocyclic group represented by $R_7$ and $R_8$ of formula (1-1) is not particularly limited as far as the heterocyclic group is a residue obtained by removing one hydrogen atom from the heterocycle ring in the heterocyclic compound, and include furanyl group, thienyl group, thienothionyl group, pyrrolyl group, imidazolyl group, N-methylimidazolyl group, thiazolyl group, oxazolyl group, pyridyl group, pyradyl group, pylimidyl group, quinolyl group, indolyl group, benzopyradyl group, benzopylimidyl group, benzothienyl group, naphtothienyl group, benzofuranyl group, benzothiazoyl group, pyridinothiazoyl group, benzoimidazolyl group, pyridinoimidazolyl group, N-methylbenzoimidazolyl group, pyridino-N-methylimidazolyl group, benzooxazolyl group, pyridinooxazolyl group, benzothiadiazolyl group, pyridinothiadiazolyl group, benzooxadiazolyl group, pyridinooxadiazolyl group, carbazolyl group, phenoxazinyl group, phenothiazinyl group. The heterocyclic group is preferably pyridyl group, imidazolyl group, and N-methylimidazolyl group, more preferably pyridyl group.

The heterocyclic group represented by $R_7$ and $R_8$ of formula (1-1) may have a substituent. The substituent connected to the heterocyclic group represented by $R_7$ and $R_8$ of formula (1-1) is not limited, but examples include alkyl group, alkoxyl group, aromatic group, heterocyclic group, halogen atom, hydroxy group, mercapto group, nitro group, alkyl-substituted amino group, aryl-substituted amino group, nonsubstituted amino group ($NH_2$ group), cyano group, and isocyano group. The substituent is more preferably alkyl group, aromatic group, heterocyclic group or halogen atom, and is especially preferably aromatic group or heterocyclic group.

Examples of the alkyl group as the substituent connected to the heterocyclic group represented by $R_7$ and $R_8$ of formula (1-1) are preferably an alkyl group having a carbon number of 1 to 20 such as methyl group, ethyl group, propyl group, iso-propyl group, n-butyl group, iso-butyl group, t-butyl group, n-pentyl group, iso-pentyl group, t-pentyl group, sec-pentyl group, n-hexyl group, iso-hexyl group, n-heptyl group, sec-heptyl group, n-octyl group, n-nonyl group, sec-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, and n-eicosyl group, more preferably an alkyl group having a carbon number of 1 to 12, further preferably an alkyl group having a carbon number of 1 to 6, especially preferably an alkyl group having a carbon number of 1 to 4.

The alkoxy group as the substituent connected to the heterocyclic group represented by $R_7$ and $R_8$ of formula (1-1) is a substituent obtained by bonding an oxygen atom with an alkyl group. Examples of the alkyl group in the alkoxy group include the same one described in the alkyl group as a substituent connected to the heterocyclic group represented by $R_7$ and $R_8$ of formula (1-1). The preferable examples of the alkyl group in the alkoxy group also include the same one described there.

The aromatic group as a substituent connected to the heterocyclic group represented by $R_7$ and $R_8$ of formula (1-1) is not limited as far as the aromatic group is a residue obtained by removing one hydrogen atom from the aromatic ring in aromatic compound. Examples include phenyl group, biphenyl group, terphenyl group, quarterphenyl group, tolyl group, indenyl group, naphthyl group, anthryl group, fluorenyl group, pyrenyl group, phenanthryl group, and mesityl group. Phenyl group, biphenyl group, terphenyl group, quarterphenyl group, naphthyl group, and anthryl group are preferable. Phenyl group, biphenyl group, terphenyl group, and naphthyl group are more preferable.

Examples of the heterocyclic group as a substituent connected to the heterocyclic group represented by $R_7$ and $R_8$ of formula (1-1) include the same one described in the heterocyclic group represented by $R_7$ and $R_8$ of formula (1-1). The preferable examples of the heterocyclic group also include the same one described there.

Examples of the halogen atom as a substituent connected to the heterocyclic group represented by $R_7$ and $R_8$ of formula (1-1) include fluorine atom, chlorine atom, bromine atom, and iodine atom. Fluorine atom and chlorine atom are preferable. Fluorine atom is more preferable.

The alkyl-substituted amino group as a substituent connected to the heterocyclic group represented by $R_7$ and $R_8$ of formula (1-1) is limited to neither monoalkyl-substituted amino group nor dialkyl-substituted amino group. Examples of the alkyl group in alkyl-substituted amino group include the same one described in the alkyl group as the substituent connected to heterocyclic group represented by $R_7$ and $R_8$ of formula (1-1). The preferable examples of the alkyl group also include the same one described there.

The aryl-substituted amino group as a substituent connected to the heterocyclic group represented by $R_7$ and $R_8$ of formula (1-1) is limited to neither monoaryl-substituted amino group nor diaryl-substituted amino group. Examples of the aryl group in aryl-substituted amino group include the same one described in the aromatic group as the substituent connected to heterocyclic group represented by $R_7$ and $R_8$ of formula (1-1) and the same one described in the heterocyclic group represented by $R_7$ and $R_8$. The preferable examples of the aryl group also include the same one described there.

The heterocyclic ring formed by connecting $R_7$ with $R_8$ of formula (1-1) is not limited as far as the heterocyclic ring has a ring structure having two or more elements. Examples include thiophene ring, furan ring, pyrrole ring, pyridine ring, imidazole ring, pyrazole ring, oxazole ring, thiazole ring, pyrazine ring, and thiazine ring. Pyridine ring, and imidazole ring are preferable. Pyridine ring is more preferable.

The heterocycle formed by connecting $R_7$ with $R_8$ of formula (1-1) may have one or more substituents.

The substituent connected to the heterocycle formed by connecting $R_7$ and $R_8$ of formula (1-1) is not limited.

Examples include the same one described in the substituent connected to the heterocyclic group represented by $R_7$ and $R_8$ of formula (1-1).

$R_7$ and $R_8$ of formula (1-1) are preferably each independently an alkyl group having a carbon number of 1 to 18 or connected to each other to form a heterocycle, more preferably connected to form a heterocycle.

$R_9$ and $R_{10}$ of formula (1-2) each independently represent an amino group or a substituted amino group. Examples of the amino group represented by $R_9$ and $R_{10}$ of formula (1-2) include alkyl-substituted amino group and aryl-substituted amino group. Specific examples include the same ones described in the alkyl-substituted amino group and the aryl-substituted amino group as a substituent connected to the heterocyclic group represented by $R_7$ and $R_8$ of formula (1-1).

$R_9$ and $R_{10}$ of formula (1-2) are preferably each independently alkyl-substituted amino group and aryl-substituted amino group, more preferably alkyl-substituted amino group.

The compound represented by formula (1) of the present invention generates a radical and a base with cleavage reaction and decarboxylation reaction by the irradiation of active energy ray as shown in the reactions described below to start radical polymerization of a polymer precursor having a radical polymerizable group. The base generated at the same of the radical can not only provide a cross-linking polymerization of a polymer precursor described below but also lower a curing starting temperature of the polymer precursor due to the catalytic action of the base.

Next, the synthetic method of the compound represented by formula (1) of the present invention will be explained.

The compound represented by formula (1) of the present invention can be synthesized by using a well-known method. For example, a paraformaldehyde is reacted with a benzoin derivative represented by formula (21) in the presence of a metal hydroxide at a room temperature for 30 minutes to produce an intermediate compound represented by formula (22-1). After that, the intermediate compound (22-1) is reacted with sodium nitrite in the presence of sulfuric acid, etc., to produce the intermediate compound represented by formula (23). Next, the intermediate compound represented by formula (23) obtained above is reacted with carbon monoxide and chlorine under a catalyst to produce an intermediate compound represented by formula (24). Lastly the intermediate compound represented by formula (24) is reacted with an amine compound to produce the compound represented by formula (1). As a purified method for the compound having high crystalline nature, a crystallization method is suitable. Alternatively, purification may be conducted by washing using a solvent. Note that the meanings of $R_1$ to $R_6$ and A in formulas (21) to (24) and in the amine compound AH are the same as those of $R_1$ to $R_6$ and A in formula (1).

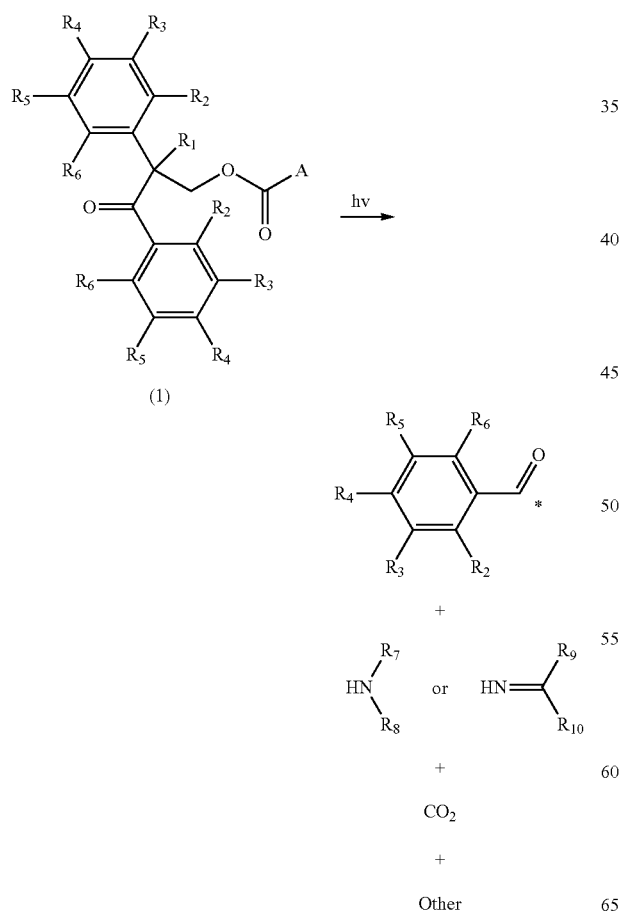

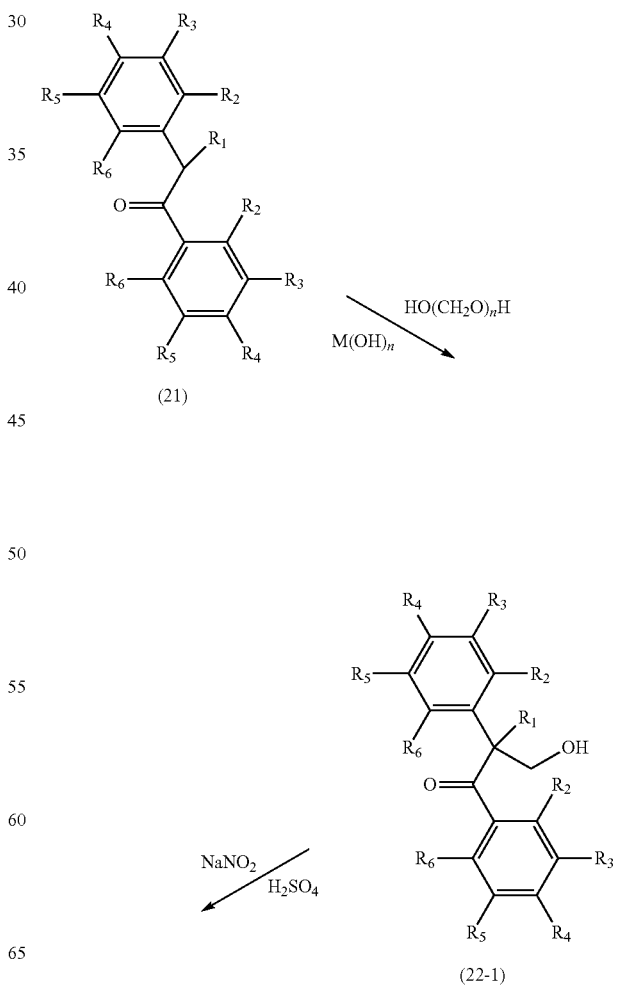

-continued

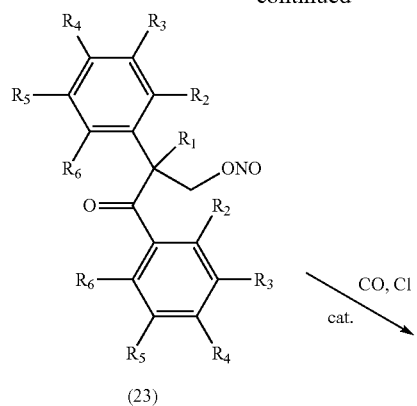

(23)

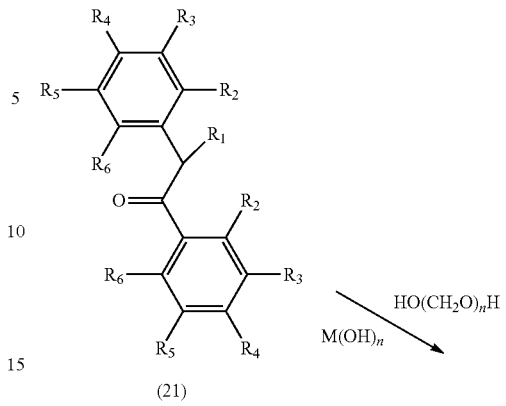

(21)

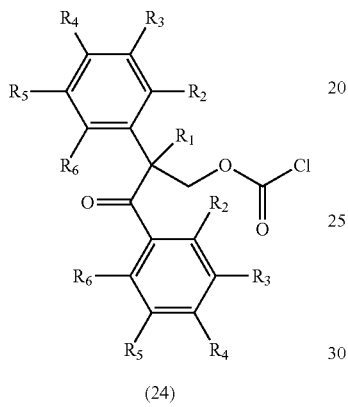

(24)

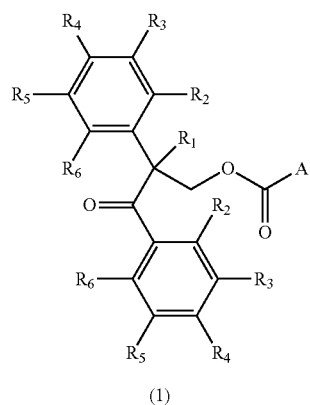

(1)

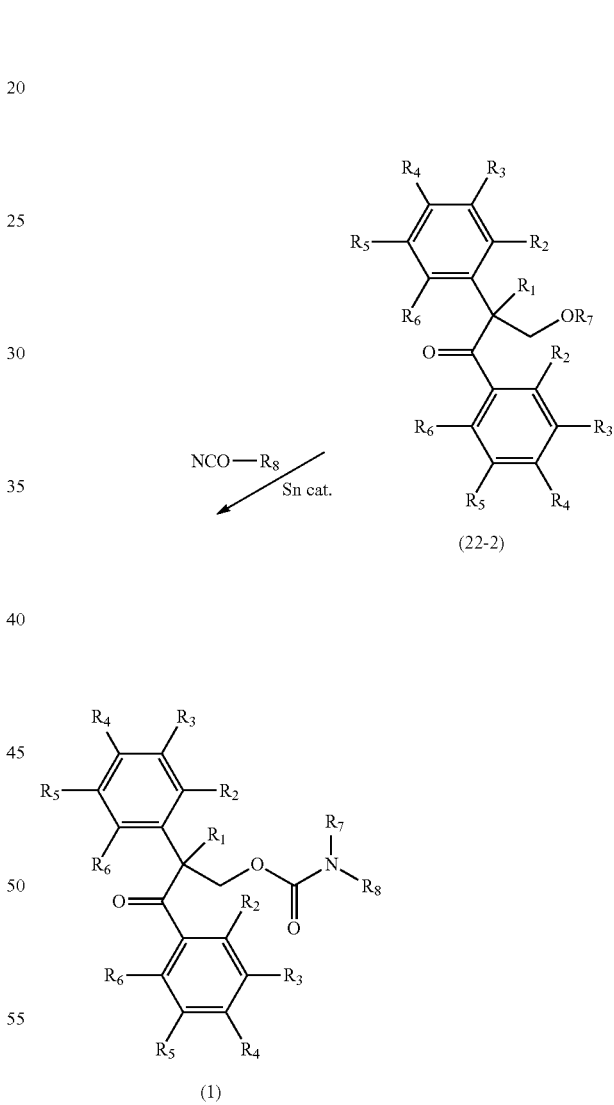

When A in formula (1) is the substituent represented by formula (1-1), by using a method disclosed in J. Photopolym. Sci. Technol 27, 2, 2014, for example, a paraformaldehyde is reacted with a benzoin derivative represented by formula (21) in the presence of a metal hydroxide at a room temperature for 30 minutes to produce an intermediate compound of formula (22-2). After that, the intermediate compound (22-2) is reacted with an isocyanate in the presence of an organic compound including tin or lead, etc., so as to obtain the compound represented by formula (1). The purified method is the same one described above. Note that the meaning of $R_1$ to $R_8$ in formulas (21) to (22-2) and an isocyanate represent the same as those of $R_1$ to $R_8$ in formula (1).

Specifically, examples of the compound represented by formula (1) are shown as formulas (a) to (i) described below, but the present invention is not limited to these compounds.

(a)
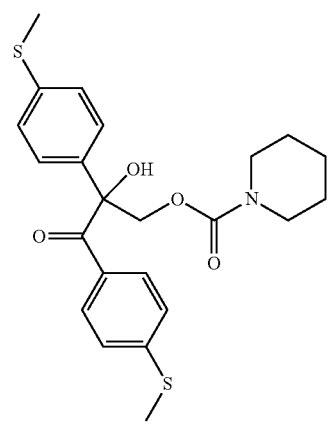
(b)
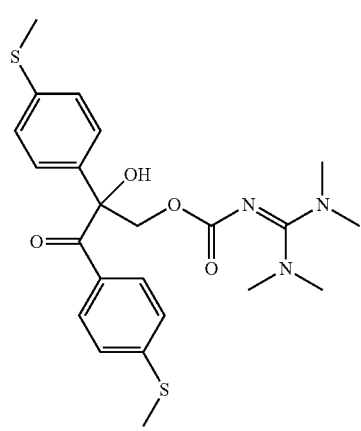
(c)
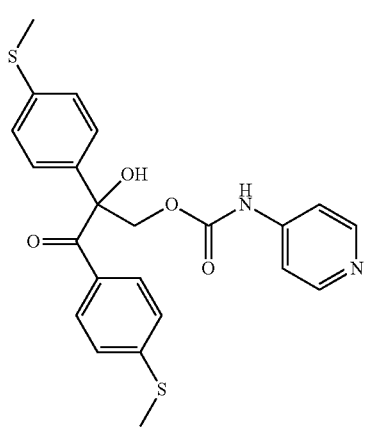
(d)
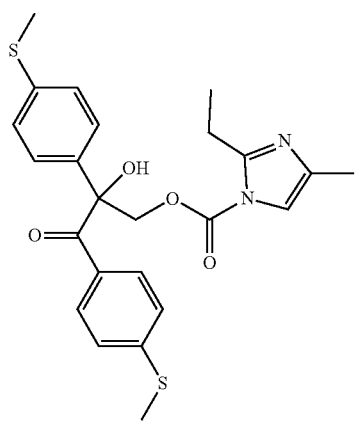
(e)
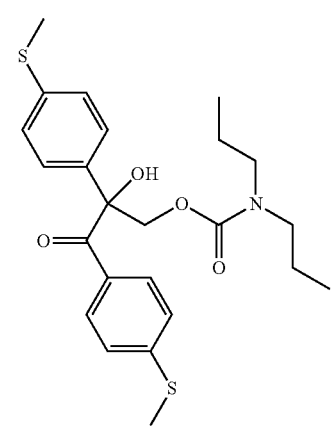
(f)
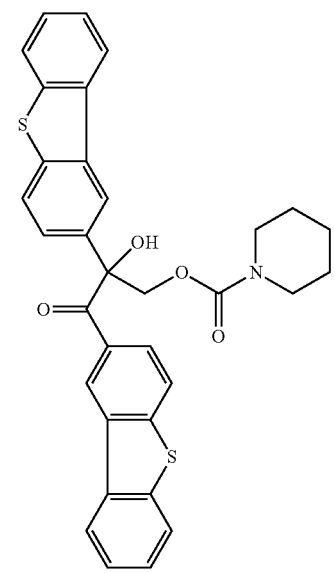

(g)

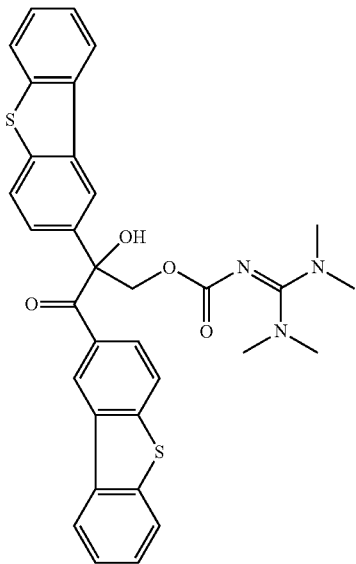

(h)

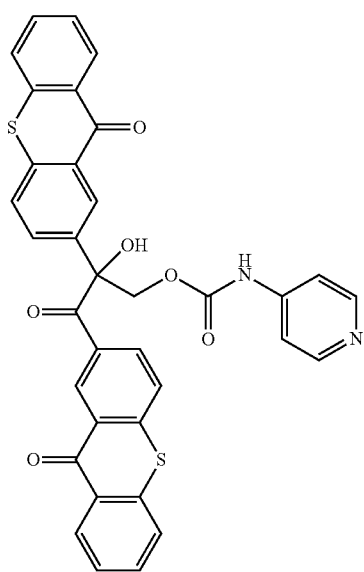

(i)

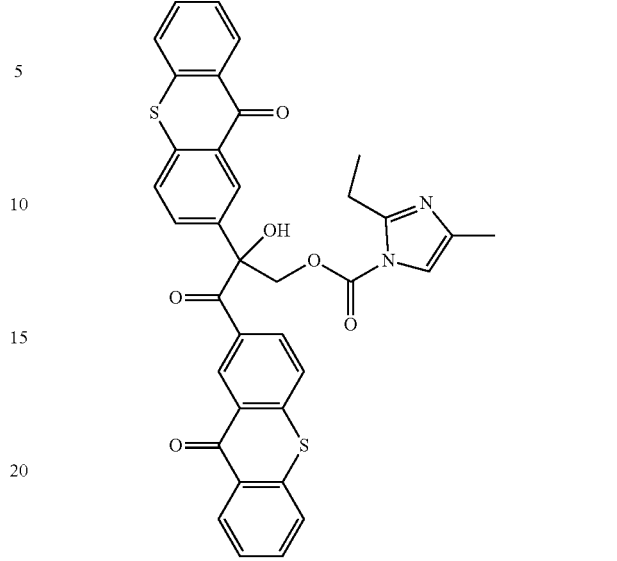

<Function of the Photopolymerization Initiator>

When the compound represented by formula (1) of the present invention is used as a photopolymerization initiator, the compound needs to have the absorption in at least part of the exposure wavelength to produce a radical and a base which can contribute sufficiently to the polymerization reaction or the condensed polymerization reaction of the polymer precursor. Because the wavelength of the high-pressure mercury vapor lamp which is a general exposure light source is 365 nm, 405 nm and 436 nm, the compound preferably has the absorption of the activity energy ray having at least one of these wavelengths. The compound having absorption in such wavelength region are preferable, in view of further increasing the kinds of applicable polymer precursors.

When the compound represented by formula (1) is used as a photopolymerization initiator, the molar absorbance coefficient is preferably 100 or more to the active energy ray having a wavelength of 365 nm, or 1 or more to the active energy ray having a wavelength of 405 nm in view of further increasing the kinds of applicable polymer precursors.

The absorbance at the wavelength region described above which the compound represented by formula (1) has can be confirmed by solving the compound in a solvent (e.g., acetonitrile) which has no absorbance in the wavelength region to make a solution having a concentration of not more than $1 \times 10^{-4}$ mol/L (usually about from $1 \times 10^{-5}$ mol/L to $1 \times 10^{-4}$ mol/L) of the base generator represented by formula (1) and measuring the absorbance of the solution by a ultraviolet and visible spectrophotometer (for example, UV-2550 manufactured by Shimazu Corporation).

The photopolymerization initiator (photobase generator) containing the compound represented by formula (1) of the present invention has various applicability because of having sensitivity superior to a conventional photobase generator. The compound may be combined with not only a polymer precursor described below which is capable of being (condensation) polymerized by a base material or by heating in the presence of a base material, but also a compound capable of changing the structure or the properties thereof by a base such as an acid-base indicator, etc., so as to obtain the photosensitive composition.

Such photosensitive compositions may be used for a paint, a printing ink, a sealant, an adhesive, a display device, a semiconductor device, an electronic part, a micro electro mechanical system (MEMS), a forming material for an optical part or an architectural part.

For example, the photopolymerization initiator can be used for an image formation media obtained by subjecting to impregnation or covering a substrate with an image formation layer including the photopolymerization initiator (photobase generator) containing the compound represented by formula (1) of the present invention and the acid-base indicator, wherein the image formation layer is exposed to produce a base from the photobase generator, which may be reacted with an acid-base indicator so as to form an image.

<Photosensitive Resin Composition>

The photosensitive resin composition of the present invention contains the photopolymerization initiator containing the compound represented by formula (1) and a polymer precursor which can be polymerized by irradiation or by irradiation and heating in the presence of the photopolymerization initiator. The pattern using the photosensitivity resin of the present invention can be formed by making the difference of the solubility of exposed areas and unexposed areas, namely, by increasing the contrast of solubility due to change of the solubility through the polymerization of the polymer precursor.

<Polymer Precursor>

The polymer precursor contained in the photosensitive resin composition of present invention means a compound capable of changing to a cured product by increasing the molecular weight by the polymerization caused by a radical or a base or by heating in the presence of a base and include so-called monomer herein as a concept. Examples of the above polymerization include polymerization between the polymer precursors caused by a radical and condensation polymerization between a polymer precursor and a base compound (e.g. amines) generated from the compound represented by formula (1). In addition, the embodiments of the photosensitive resin composition of the present invention also include a case that the base compound generated from the compound represented by formula (1) works as a catalyst to lower the reaction start temperature of heat curing. The molecular weight as the polymer precursor is not limited to, but preferably about 500 to 10,000 of a weight (or a number) average molecular weight.

The polymer precursor contained in the photosensitive resin composition of present invention is not particularly limited, as far as the polymer precursor is a compound capable of increasing a molecular weight by polymerization caused by a radical generated from the compound represented by formula (1), a compound capable of (condensation) polymerization by a base material generated from the compound represented by a formula (1) or by heating in the presence of a base material, and a compound capable of lowering the reaction start temperature of (condensation) polymerization by act as a catalyst of a base compound. Examples of the polymer precursor are described below, but the polymer precursor contained in the photosensitive resin composition of the present invention is not limited to these.

<Polymer Precursor Providing Polymer by Radical Polymerization>

Examples of the polymer precursor capable of increasing molecular weight by polymerization caused by a radical generated from the compound represented by formula (1) include a compound having a substituent having radical polymerization properties. The compound having one or more substituents having radical polymerization properties is preferably a compound having a double bond in the molecule thereof, and is preferably a compound having an allyl group, an acryloyl group, a methacryloyl group or a maleimide group.

As a compound having a maleimide group, the known compound having one or more maleimide groups in the molecule can be used. Examples include an aliphatic/alicyclic maleimide resin and an aromatic maleimide resin.

Specifically, examples include N-methylmaleimide, N-ethylmaleimide, N-propylmaleimide, N-hexylmaleimide, N-cyclohexylmaleimide, maleimide-carboxylic acid, N-phenylmaleimide, N-methylphenylmaleimide, a multifunctional maleimide compound obtained by reacting maleic anhydride with 3,4,4'-triaminodiphenylmethane, triaminophenol etc., maleimide compounds obtained by reacting maleic anhydride with tris(4-aminophenyl)phosphate, tris(4-aminophenyl)thiophosphate, a trismaleimide compound such as tris(4-maleimidephenyl)methane, tetramaleimide compound such as maleimide obtained by reacting maleic anhydride with bis(3,4-dimaleimidephenyl)methane, tetramaleimide benzophenone, tetramaleimide naphthalene, triethylenetetramine, phenol novolac-type maleimide resin, isopropylidenbis(phenoxyphenylmaleimide)phenylmaleimidearalkyl resin, a biphenylene type phenylmaleimidearalkyl resin represented by formula (2), a polymaleimide represented by the polymaleimide represented by formula (3) or (4), a polymaleimide of the polyaniline obtained by condensing benzenedialdehyde and aniline. A polyaminopolymaleimide resin obtained by adding aromatic diamine to these polymaleides can also be used. Furthermore, because of molecular weight distribution, a novolak-type maleimide resin has high varnish stability and is suitable to be kneaded with a benzoxazine resin. These maleimides which are commercially available may be used. The maleimide also can be prepared using known techniques.

Examples of the compound having an allyl group include a monomer having at least two allyl groups (two or more allyl groups) in the molecular, or a copolymer having at least two allyl groups (two or more allyl groups) in the monomer unit. Examples include dicarboxylic acid diallylester such as diallylorthophthalate, diallylisophthalate and diallylterephthalate, a monomer such as triallylcyanurate, tetramethylolmethanetetraacrylate and trimelliticacidtriallylester.

Examples of the homopolymerized product of the monomer (for example the polymer obtained by polymerizing a great number of the monomers with one double bond in the monomer) include a polymer of trimelliticacidtriallylester (weight average molecular weight (Mw) is $2 \times 10^4$ and the ratio of weight average molecular weight to number average molecular weight (Mw/Mn degree) is 1.8 (dispersion).) and a polymer of triallylcyanurate (Mw=$2.8 \times 10^4$, Mw/Mn=1.5). Examples of the copolymerized product of at least two of the monomers include the copolymer of triallylcyanurate or triallylisocyanurate with dicarboxylicaciddiallylester such as a copolymer (Mw=15,000 to 18,000, Mw/Mn=1.5 to 1.6, iodine value=65 to 70, copolymer mole ratio=0:1 to 1:1) of triallylcyanurate or triallylisocyanurate with diallylphthalate (at least one of diallylester of ortho, iso, terephthalic acid). The weight average molecular weight of the homopolymer and the copolymer is preferably 2,000 to 100,000. When the weight average molecular weight is less than 2,000, the degree of improvement in drying touch property may decrease. When the weight molecular weight exceeds 100,000, development property in a diluted alkali aqueous solution may decrease. Among them, triallylisocyanurate or the homopolymer or the copolymer of triallylisocyanurate is preferable.

Specifically, examples of the compound having an acryloyl group or a methacryloyl group (provided that a compound having an epoxy group is excluded) include a diacrylate of diol such as 1,4-butanediol diacrylate, 1,6-hexanediol diacrylate, 1,9-nonanediol diacrylate and 1,10-decanediol diacrylate; a diacrylate of glycol such as ethyleneglycol diacrylate, diethyleneglycol diacrylate, triethyleneglycol diacrylate, tetraethyleneglycol diacrylate, polyethyleneglycol diacrylate, dipropyleneglycol diacrylate, tripropylene glycol diacrylate, polypropyleneglycol diacrylate, neo-pentyl glycol diacrylate; diacrylate of a diol obtained by adding at least one of ethylene oxide and propylene oxide to neopentylglycol and caprolactone modification hydroxypivalic acid neopentylglycol diacrylate; and a diacrylate having a ring structure such as a diacrylate of EO adduct of bisphenol A, a diacrylate of PO adduct of bisphenol A, tricyclodecandimethanol diacrylate, hydrogenated dicyclopentadienyl diacrylate and cyclohexyl diacrylate.

Specifically, examples of the commercial products of the compound having an acryloyl group or a methacryloyl group include LIGHTACRYLATE 1,6HX-A, 1,9ND-A, 3EG-A and 4EG-A (all are product names, manufactured by Kyoeisha chemical Co., Ltd.); HDDA, 1,9-NDA, DPGDA and TPGDA (all are product names, manufactured by Daicel-Allnex LTD.), BSCOAT #195, #230, #230D, #260, #310HP, #335HP and #700HV (all are product names, manufactured by OSAKA ORGANIC CHEMICAL INDUSTRY LTD.), ALLONICS M-208, M-211B, M-220, M-225, M-240, M-270 (all are product names, manufactured by Toagosei Company, Limited.).

Among them, from the viewpoint of the viscosity and the compatibility with the compound represented by formula (1), a diacrylate having an alkyl chain having a carbon number of 4 to 12, particularly, 1,4-butanediol diacrylate, 1,6-hexanediol diacrylate, 1,9-nonanediol diacrylate or 1,10-decanediol diacrylate is preferred.

<Polymer Precursor Providing Polymer by Intermolecular Reaction>

Examples of a polymer precursor capable of increasing molecular weight by intermolecular reaction by a base material generated from the compound represented by formula (1) or by heating in the presence of the base material include a compound having a substituent capable of reacting with the base material or a compound capable of increasing molecular weight by reaction (cross-linking reaction) for forming a bond between molecules by heating in the presence of the base material. Examples of the substituent capable of reacting with the base material and the substituent capable of reacting for forming a bond between molecules by heating in the presence of the base material include an epoxy group, an oxetane group, a thiirane group, an isocyanate group, a hydroxy group, and a silanol group. In the polymer precursor, a compound having a substituent capable of performing hydrolysis and polycondensation (for example, polysiloxane precursor) is included. Examples of the substituent capable of performing hydrolysis and polycondensation between molecules include —SiX of a polysiloxane precursor wherein the X is a hydrolysable group selected from the group consisting of an alkoxy group, an acetoxy group, an oxime group, an enoxy group, an amino group, an aminoxy group, an amide group and a halogen.

Examples of the compound having a substituent capable of reacting with a base material include a compound having at least one substituents mentioned above, for example, a compound having one or more of epoxy groups in the molecule, a compound having one or more oxetane groups in the molecule and a compound having one or more thiirane groups in the molecule.

The compound having an epoxy group is specifically explained below, but a compound having an oxetane group or a thiirane group can be used in the same manner.

<Compound Having Epoxy Group>

The compound having one or more epoxy groups in the molecule is not particular limited and the conventional compound can be used, as long as the compound has one or more epoxy groups.

Also, the photopolymerization initiator containing the compound represented by formula (1) of the present invention usually works as a curing catalyst for the compound having one or more epoxy groups in the molecular.

When the compound having one or more epoxy groups in the molecule is used, a compound having two or more functional groups having the reactivity with the epoxy group may be used together. Examples of the functional group having the reactivity with an epoxy group include a carboxyl group, a phenolic hydroxy group, a mercapto group, and a primary or a secondary aromatic amino group. Examples of the compound having two or more functional groups having the reactivity with an epoxy group in the molecule include a compound having a weight average molecular weight of 3,000 to 100,000 wherein the functional group is introduced into the polymer side chain. The embodiment where this compound is used together is one of the preferred embodiments. When the weight average molecular weight of the polymer is less than 3,000, the strength of the film decreases, and tuck (sticky) occurs on the surface of the cured film resulting in easy adherence of impurity to the cured film. When the weight average molecular weight of the polymer is more than 100,000, the viscosity at the time of solving the polymer in a solvent or the melt viscosity may increase.

Examples of the compound having one or more epoxy groups in the molecule include a bisphenol A-type epoxy resin derived from a bisphenol A and an epichlorohydrin, a bisphenol F-type epoxy resin derived from a bisphenol F and an epichlorohydrin, a bisphenol S-type epoxy resin, a phenol novolac-type epoxy resin, a cresol novolac-type epoxy resin, a bisphenol A novolac-type epoxy resin, a bisphenol F novolac-type epoxy resin, an alicyclic-type epoxy resin, a diphenyl ether-type epoxy resin, a hydroquinone-type epoxy resin, a naphthalene-type epoxy resin, a biphenyl-type epoxy resin, a fluorene-type epoxy resin, a multifunctional-type epoxy resin such as trifunctional-type epoxy resin or tetrafunctional-type epoxy resin, a glycidyl ester-type epoxy resin, a glycidylamine-type epoxy resin, a hydantoin-type epoxy resin, an isocyanurate-type epoxy resin, and an aliphatic chain epoxy resin. These epoxy resins may be halogenated or hydrogenated. Examples of the epoxy resin which is commercially available include jER 828, 1001, 801N, 806, 807, 152, 604, 630, 871, YX8000, YX8034 and YX4000 (all are manufactured by Mitsubishi Chemical Corporation), EPICLON 830, EXA835LV, HP4032D and HP820 (all are manufactured by DIC Corporation), EP4100 series, EP4000 series, EPU series (all are manufactured by ADEKA Co., Ltd.), CELLOXYIDE series (2021, 2021P, 2083, 2085, and 3000, etc.) EPOLEAD series and EHPE series, (all are manufactured by DICEL Corporation), YD series, YDF series, YDCN series and YDB series (all are manufactured by Tohto kasei Co., Ltd.), DENACOL series (manufactured by NAGASE Chemtex Corporaton), Epolite series (manufactured by Kyoei chemical Co., Ltd), but the compound is not particularly limited to these. Two or more of these epoxy resins may be used together. Not only because several grades having different molecular weights are widely available, but also because adhesive properties or reactivity may be optionally selected, the bisphenol-type epoxy resin is preferred.

<Compound Having Oxetane Group>

Examples of the compound having one or more oxetane groups in the molecule include multi-functional oxetane compounds such as difunctional oxetane compound such as 4,4'-(3-ethyloxetane-3-yl-methyloxymethyl)biphenyl (OXBP), 3-ethyl-3-hydroxymethyloxetane (EHO), 1,4-bis[{(3-ethyl-3-oxetanyl)methoxy}methyl]benzene (XDO), di[1-ethyl-(3-oxetanyl)]methylether (DOX), di[1-ethyl-(3-oxetanyl)]methylether (DOE), 1,6-bis[(3-ethyl-3-oxetanyl) methoxy]hexane (HDB), 9,9-bis[2-methyl-4-{2-(3-oxetanyl)butoxy phenyl]fluorene, 9,9-bis[4-[2-{2-(3-oxetanyl)}butoxy]ethoxyphenyl]fluorene, and an oxetanated novolac resin.

<Compound Having Thiirane Group>

Examples of the compound having one or more thiirane groups in the molecule include a compound having one or more thiirane rings in the molecule, for example, bis(2,3-epithiopropyl)sulfide, bis(2,3-epithiopropylthio)ethane, bis(2,3-epithiopropylthio)propane, bis(2,3-epithiopropylthio) butane, bis(5,6-epithio-3-thiohexane)sulfide, bis(2,3-epithiopropyl)disulfide, bis(3,4-epithiobutyl)disulfide, bis (4,5-epithiopentyl)disulfide and bis(5,6-epithiohexyl) disulfide. Bis(2,3-epithiorpropyl)sulfide and bis(2,3-epithiopropyl)disulfide are particularly preferred.

Examples of the compound performing cross-linking reaction between molecules include a combination of a compound having two or more isocyanate groups in the molecule with a compound having two or more hydroxy groups in the molecule. By reaction of the isocyanate groups with the hydroxy groups, a urethane bond between the molecules are formed to make a polymer.

<Compound Having Isocyanate Group>

The compound having two or more isocyanate groups in the molecule is not particularly limited as long as the compound has two or more isocyanate groups in the molecule. The conventional one can be used. Examples of such compounds include low molecular weight compounds represented by p-phenylene diisocyanate, 2,4-toluene diisocyanate, 2,6-toluene diisocyanate, 1,5-naphthalene diisocyanate, hexamethylene diisocyanate as well as an oligomer and a compound having a weight average molecular weight of 3,000 or more, of which the side chain or the terminal part has an isocyanate group.

<Compound Having Hydroxy Group>

The compound having two or more hydroxy groups are usually used in combination with a compound having an isocyanate group in the molecule. The compound having a hydroxy group is not particularly limited, as long as the compound has two or more hydroxy groups in the molecule. Examples of such compounds include a small molecular weight compound such as ethylene glycol, propylene glycol, glycerin, diglycerine and pentaerythritol, as well as a compound of which the side chain or the terminal part has a hydroxy group, which is a compound has a weight average molecular weight of 3,000 or more.

<Polysiloxane Precursor>

Examples of the compound performing hydrolysis and polycondensation between the molecules also include a polysiloxane precursor. Examples of the polysiloxane precursor include an organic silicon compound represented by $Y_nSiX_{(4-n)}$ (wherein, Y represents an alkyl group, a fluoroalkyl group, a vinyl group or a phenyl group which may have substituent or hydrogen, and X represents a hydrolysable group selected from the group consisting of an alkoxy group, an acetoxy group, an oxime group, an enoxy group, an amino group, an aminoxy group, an amido group and a halogen atom. n shows an integer of 0 to 3.) and the hydrolysis polycondensation products of the organic silicon compound. In formula $Y_nSiX_{(4-n)}$, n is preferably 0 to 2. From a viewpoint of easily preparing a silica dispersion oligomer solution and easy availability, the hydrolysable group is preferably an alkoxy group. The organic silicon compound mentioned above is not particularly limited, and the conventional one can be used. Examples of the organic silicon compound include trimethoxysilane, triethoxysilane, methyltrichlorosilane, methyltrimethoxysilane, methyltriethoxysilane, methyltriisopropoxysilane, methyltri-t-butoxysilane, ethyltribromosilane, ethyltrimethoxysilane, ethyltriethoxysilane, n-propyltriethoxysilane, n-hexyltrimethoxysilane, phenyltrimethoxysilane, phenyltriethoxysilane, tetramethoxysilane, tetraethoxysilane, tetrabutoxysilane, dimethoxydiethoxysilane, dimethyldichlorosilane, dimethyldimethoxysilane, diphenyldimethoxysilane, vinyltrimethoxysilane, trifluoropropyltrimethoxysilane, γ-glycidoxypropylmethyldiethoxysilane, γ-glycidoxypropyltrimethoxysilane, γ-methacryloxypropylmethyldimethoxysilane, γ-aminopropylmethyldimethoxysilane, γ-mercaptopropylmethyldiethoxysilane, γ-mercaptopropyltrimethoxysilane, β-(3,4-epoxycyclohexyl)ethyltrimethoxysilane, fluoroalkylsilane known as a fluorine silane coupling agent and the hydrolysis condensate or the cohydrolysis condensate thereof, and the mixtures thereof.

<Polymer Precursor Providing Polymer by Ring Closure Reaction in Molecule>

Examples of the polymer precursor capable of increasing the molecular weight by the ring closure reaction in the molecule include a polyimide precursor, a polybenzoxazole precursor. These precursors may be a mixture of two or more polymer precursors.

The polyimide precursor and the polybenzoxazole precursor which are the preferable polymer precursor in the present invention are explained below, but the present invention is not particularly limited.

<Polyimide Precursor>

For a polyimide precursor, a polyamic acid having a repeating unit represented by the following formula (8) is preferably used. In formula (8), $R_{11}$ is a tetravalent organic group. $R_{12}$ is a divalent organic group. $R_{13}$ and $R_{14}$ are a hydrogen atom or an organic group. n is natural number of 1 or more. Examples of the organic group of $R_{13}$ and $R_{14}$ include an alkyl group, an alkenyl group, an alkynyl group, an aryl group and a structure having an ether bond, represented by $C_nH_{2n}OC_mH_{2m+1}$.

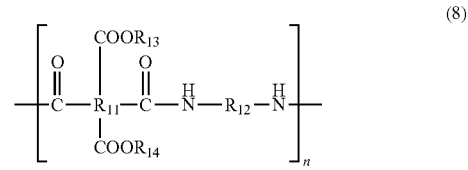

(8)

A polyamic acid is preferred, because the polyamic acid can be synthesized just by mixing a dianhydride with a diamine in a solution, that is, through one step reaction, and further can be obtained in simple synthesis at a low cost.

When the polymer precursor is a polyamic acid having a repeating unit represented by formula (8), the temperature required for imidization can be lowered to usually less than 300° C., preferably 250° C. or less due to the catalyst effects of the base material. Note that when the general polyamic acid is used, the imidization requires a high temperature of 300° C. or higher. Therefore, the application of the products using the general polyamic acid is limited. However, because the temperature required for imidization can be lowered in the present invention, the products can be applied to more various applications.

For a method for manufacturing a polyimide precursor, the conventional technique can be used. Examples of the method include a method for synthesizing the polyamide acid which is a precursor from a dianhydride and a diamine, a method where a diamino compound or the derivative thereof is reacted with an ester acid or a carboxylic acid of an amide acid monomer obtained by reacting a dianhydride with a monohydric alcohol, an amino compound, or an epoxy compound, etc., but the method is not limited to these examples.

<Polybenzoxazole Precursor>

For a polybenzoxazole precursor, a polyamide alcohol having a repeating unit represented by the following formula (9) is preferably used.

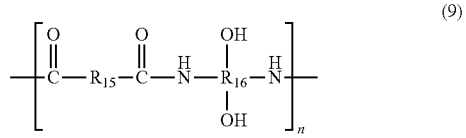

(9)

In formula (9), $R_{15}$ is a divalent organic group, and $R_{16}$ is a tetravalent organic group. n is natural number of 1 or more. The polyamide alcohol having a repeating unit represented by formula (9) may contain a single repeating unit or two or more repeating units.

Examples of a dicarboxylic acid and the derivatives thereof which are applicable to the reaction for obtaining the polybenzoxazole precursor mentioned above include phthalic acid, isophthalic acid, terephthalic acid, 4,4'-benzophenonedicarboxylic acid, 3,4'-benzophenonedicarboxylic acid, 3,3'-benzophenonedicarboxylic acid, 4,4'-biphenyldicarboxylic acid, 3,4'-biphenyldicarboxylic acid, 3,3'-biphenyldicarboxylic acid, 4,4'-diphenyletherdicarboxylic acid, 3,4'-diphenyletherdicarboxylic acid, 3,3'-diphenyletherdicarboxylic acid, 4,4'-diphenylsulfonedicarboxylic acid, 3,4'-diphenylsulfonedicarboxylic acid, 3,3'-diphenylsulfonedicarboxylic acid, 4,4'-hexafluoroisopropylidenedibenzoic acid, 4,4'-dicarboxy diphenylamide, 1,4-phenylenediethanoic acid, 1,1-bis(4-carboxyphenyl)-1-phenyl-2,2,2-trifluoroethane, bis(4-carboxyphenyl) tetraphenyldisiloxane, bis(4-carboxyphenyl) tetramethyldisiloxane, bis(4-carboxyphenyl)sulfone, bis(4-carboxyphenyl)methane, 5-t-butylisophthalic acid, 5-bromoisophthalic acid, 5-fluoroisophthalic acid, 5-chloroisophthalic acid, 2,2-bis(p-carboxyphenyl)propane, 4,4'-(p-phenylenedioxy)dibenzoic acid, 2,6-naphthalenedicarboxylic acid or an acid halide thereof and an active ester thereof with a hydroxydibenzotriazole, but is not limited to these examples. These are used alone or in combination of two or more.

Specifically, examples of a hydroxydiamine which is applicable to reaction for obtaining the polybenzoxazole precursor include 3,3'-dihydroxybenzidine, 3,3'-diamino-4,4'-dihydroxybiphenyl, 4,4'-diamino-3,3'-dihydroxybiphenyl, 3,3'-diamino-4,4'-dihydroxydiphenylsulfone, 4,4'-diamino-3,3'-dihydroxydiphenylsulfone, bis-(3-amino-4-hydroxyphenyl)methane, 2,2-bis-(3-amino-4-hydroxyphenyl)propane, 2,2-bis-(3-amino-4-hydroxyphenyl)hexafluoropropane, 2,2-bis-(4-amino-3-hydroxyphenyl)hexafluoropropane, bis-(4-amino-3-hydroxyphenyl)methane, 2,2-bis-(4-amino-3-hydroxyphenyl)propane, 4,4'-diamino-3,3'-dihydroxybenzophenone, 3,3'-diamino-4,4'-dihydroxybenzophenone, 4,4'-diamino-3,3'-dihydroxydiphenylether, 3,3'-diamino-4,4'-dihydroxydiphenylether, 1,4-diamino-2,5-dihydroxybenzene, 1,3-diamino-2,4-dihydroxybenzene, 3-diamino-4,6-dihydroxybenzen, but is not particularly limited. These compounds are used alone or in combination of two or more.

In order to increase the sensitivity and to obtain a pattern form which accurately provides a mask pattern when made into the photosensitivity resin composition, the transmittance of the polymer precursor such as the polyimide precursor and the polybenzoxazole precursor, etc., is preferably 5% or more, more preferably 15% or more to the exposure wavelength at the thickness of 1 µm. High transmittance of the polymer precursor such as the polyimide precursor or the polybenzoxazole precursor, etc., to the exposure wavelength means low loss of the active energy ray, which provides the photosensitive resin composition having the high sensitivity.

Also, when the exposure is performed by using a high-pressure mercury-vapor lamp which is a general exposure source, the transmittance to an active energy ray which has at least one of the wavelengths of 436 nm, 405 nm and 365 nm is preferably 5% or more, further preferably 15% or more, especially preferably 50% or more, when the film has a thickness of 1 µm.

The weight average molecular weight of the polymer precursor such as the polyimide precursor or the polybenzoxazole precursor, although it depends on the application, is preferably in the range of 3,000 to 1,000,000, more preferably in the range of 5,000 to 500,000, further preferably in the range of 10,000 to 500,000. When the weight average molecular weight is less than 3,000, the strength of the coat or the film obtained from the polymer precursor is insufficient. In addition, when the polymer such as the polyimide is made by heating treatment, etc., the strength of the resultant film is poor. On the other hand, when the weight average molecular weight exceeds 1,000,000, the viscosity increases and the solubility decreases. As a result, the coat or the film having a flat surface and a uniform thickness is difficult to be obtained.

The molecular weight used herein is meant to be a value obtained by the polystyrene conversion using a gel permeation chromatography (GPC). The molecular weight may be a molecular weight of a polymer precursor itself such as a polyimide precursor, etc., or a molecular weight of a polymer precursor after chemical imidization treatment by using acetic anhydride, etc.

A solvent used in the synthesis of the polyimide precursor or the polybenzoxazole precursor is preferably a polar solvent. Examples of the typical solvent include N-methyl-2-pyrrolidone, N-acetyl-2-pyrrolidone, N,N-dimethylformamide, N,N-dimethylacetamide, N,N-diethylformamide, N,N-diethylacetamide, N,N-dimethylmethoxyacetamide, dimethyl sulfoxide, hexamethylphosphoamide, pyridine, dimethylsulfone, tetramethylenesulfone, dimethyltetramethylenesulfone, diethyleneglycoldimethylether, cyclopentanone, γ-butyrolactone, α-acetyl-γ-butyrolactone, etc. These solvents are used alone or in combination of two or more. In addition to the above, examples of a usable solvent for combination include a nonpolar solvent such as benzene, benzonitrile, 1,4-dioxane, tetrahydrofuran, butyrolactone, xylene, toluene, cyclohexanone, etc. These solvents are used as a disperse medium of material, a reaction conditioning agent, or a volatilization controlling agent for a solvent from a product, and a coating smoothing agent, etc.

The polyamic acid and the polybenzoxazole precursor also have an advantage at the point that the difference between the solubility of the exposed region and the solubility of the unexposed region in the photosensitive resin composition of the present invention is made larger by combination of decrease of solubility due to the base material generated from the photopolymerization initiator containing the compound represented by formula (1), because the base material works to increase the molecular weight so as to lower the solubility.

The photosensitive resin composition of the present invention can include one or more polymer precursors. The content of the polymer precursor (the total content of the polymer precursor, when several polymer precursors are used) in the photosensitive resin composition of the present invention is preferably 30% by mass or more, more preferably 50% by mass or more, to the whole solid content of the photosensitive resin composition, in view of the film properties, particularly, the film strength and the heat resistance.

Also, the content of the photopolymerization initiator containing the compound represented by formula (1) in the photosensitive resin composition of the present invention is usually 0.1 to 95% by mass, preferably 0.5 to 60% by mass to the whole solid content of the polymer precursor included in the photosensitive resin composition. When the content of the photopolymerization initiator is less than 0.1% by mass, the large difference between the solubility of the exposed region and the solubility of the unexposed region is not sufficiently made. When the content of the photosensitive resin composition exceeds 95% by mass, the properties of the cured products of the photosensitive resin composition are difficult to occur. When the base compound generated by irradiation from the photopolymerization initiator containing the compound represented by formula (1) is used as a curing agent, for example, at a case using an epoxy compound together, the content of the photopolymerization initiator containing the compound represented by formula (1) is usually 0.1 to 95% by mass, preferably 0.5 to 60% by mass to the whole solid content of the polymer precursor contained in the photosensitive resin composition.

When a base compound generated from the compound represented by formula (1) works as a catalyst, the content of the photopolymerization initiator containing the compound represented by formula (1) is usually 0.1 to 30% by mass, preferably 0.5 to 20% by mass to the whole solid content of the polymer precursor contained in the photosensitive resin composition.

<Other Components>

The photosensitive resin composition of the present invention may be a simple mixture of the photopolymerization initiator containing the compound represented by formula (1) and the polymer precursor, but may further contain other components such as a solvent, a photocurable or a thermosetting component, and a non-polymeric binder resin except for the polymer precursor.

As a solvent for dissolving, dispersing or dilute the photosensitive resin composition, various general-purpose solvents can be used. Also, when polyamide acid is used as a polymer precursor, the solution provided by a synthesis reaction of the polyamide acid may be just used as it is and may be mixed with the photopolymerization initiator including the compound represented by formula (1), and optional other components as necessary.

Examples of the available solvent used widely include ethers such as diethyl ether, tetrahydrofuran, dioxane, ethylene glycol dimethyl ether, ethylene glycol diethyl ether, propylene glycol dimethyl ether, propylene glycol diethyl ether and diethylene glycol dimethyl ether; glycol monoethers (so-called cellosolves) such as ethylene glycol monomethyl ether, ethylene glycol monoethyl ether, propylene glycol monomethyl ether, propylene glycol monoethyl ether, diethylene glycol monomethyl ether and diethylene glycol monoethyl ether; ketones such as methyl ethyl ketone, acetone, methyl isobutyl ketone, cyclopentanone and cyclohexanone; esters such as ethylacetate, butylacetate, n-propylacetate, i-propylacetate, n-butylacetate, i-butylacetate, ester acetate of glycolmonoeters (e.g., methyl cellosolve acetate, ethyl cellosolve acetate), propylene glycol monomethyl ether acetate, propylene glycol monoethyl ether acetate, dimethyl oxalate, methyl lactate and ethyl lactate; alcohols such as ethanol, propanol, butanol, hexanol, cyclohexanol, ethylene glycol, diethylene glycol and glycerin; halogenated hydrocarbons such as methylene chloride, 1,1-dichloroethane, 1,2-dichloroethylene, 1-chloropropane, 1-chlorobutane, 1-chloropentane, chlorobenzene, bromobenzene, o-dichlorobenzene and m-dichlorobenzene; amides such as N,N-dimethylformamide, N,N-diethylformamide, N,N-dimethylacetamide, N,N-diethyl acetamide and N,N-dimethylmethoxyacetamide; pyrrolidones such as N-methyl-2-pyrrolidone and N-acetyl-2-pyrrolidone; lactones such as γ-butyrolactone and α-acetyl-γ-butyrolactone; sulfoxides such as dimethyl sulfoxide; sulfones such as dimethyl sulfone, tetramethylene sulfone and dimethyl tetramethylene sulfone; phosphate amides such as hexamethyl phosphoamide, other organic polarity solvents. Besides, aromatic hydrocarbons such as benzene, toluene, xylene, pyridine, and other organic non-polar solvents may be used. These solvents are used alone or in combination.

Among them, polar solvents such as propylene glycol monomethyl ether, methyl ethyl ketone, cyclopentanone, cyclohexanone, ethylacetate, propylene glycol monomethyl ether acetate, N,N-dimethyl acetamide, N-methyl-2-pyrrolidone and γ-butyrolactone; aromatic hydrocarbons such as toluene; and mixed solvents containing these solvents are preferably used.

In the photosensitive resin composition of the present invention, a photocurable component may be used together. As a photocurable component, a compound having one or two or more ethylenically unsaturated bonds may be used. Examples of the photocurable component include amide monomer, (meta)acrylate monomer, urethane(meta)acrylate oligomer, polyester(meta)acrylate oligomer, epoxy(meta)acrylate, and hydroxy group containing (meta)acrylate, aromatic series vinyl compounds such as styrene. In a case where the polyimide precursor has a carboxylic component such as polyamic acid in the structure, an ionic bond is formed by the compound having the ethylenically unsaturated bond having a tertiary amino group with the carboxylic acid of the polyimide precursor so as to make the large contrast of the solubility speeds of the exposed region and the unexposed region in the photosensitive resin composition.

In the photosensitive resin composition of the present invention, a photopolymerization initiator (photobase generator) except for the photopolymerization initiator containing the compound represented by formula (1) may be used together.

The photopolymerization initiator which can be used together is not particularly limited, for example, a light radical polymerization initiator may be used. As a light radical polymerization initiator, any compounds may be used as far as the compound may provide a radical by light, laser, electron beam, etc., to start the radical polymerization reaction.

Examples of the photopolymerization initiator which can be used together include benzoin and benzoin alkyl ethers such as benzoin, benzoin methyl ether, benzoin ethyl ether and benzoin isopropyl ether; alkyl phenones such as 2-hydroxy-2-methyl-1-phenyl-propan-1-one; acetophenones such as acetophenone, 2,2-dimethoxy-2-phenyl acetophenone, 2,2-diethoxy-2-phenylacetophenone, and 1,1-dichloroacetophenone; aminoacetophenones such as 2-methyl-1-[4-(methylthio)phenyl]-2-morpholinopropan-1-one, 2-benzyl-2-dimethylamino-1-(4-morpholinophenyl)-butan-1-one and N,N-dimethylaminoacetophenone; anthraquinones such as 2-methylanthraquinone, 2-ethylanthraquinone, 2-t-butylanthraquinone and 1-chloroanthraquinone; thioxanthones such as 2,4-dimethylthioxanthone, 2,4-diethylthioxanthone, 2-chlorothioxanthone, and 2,4-diisopropylthioxanthone; ketals such as acetophenone dimethylketal and benzyldimethylketal; 2,4,5-triarylimidazole dimer; riboflavin tetrabutylate; thiol compounds such as 2-mercaptobenzimidazole, 2-mercaptobenzoxazole and 2-mercaptobenzothiazole; organohalogens such as 2,4,6-tris-s-triazine, 2,2,2-tribromoethanol and tribromomethylphenyl sulfone; benzophenones or xanthones such as benzophenone and 4,4'-bisdiethylamino benzophenone; acylphosphine oxides such as 2,4,6-trimethylbenzoyldiphenylphosphine oxide and bis(2,4,6-trimethylbenzoyl)-phenylphosphine oxide; titanocenes such as bis(cyclopentadienyl)diphenyl titanium, bis(cyclopentadienyl)dichlorotitanium, bis(cyclopentadienyl)-bis(2,3,4,5,6-pentafluorophenyl) titanium and bis(cyclopentadienyl)-bis(2,6-difluoro-3-(pyrrol-1-yl)phenyl) titanium.

These photopolymerization initiators can be used alone or as a mixture of two or more, besides, photoinitiating aids such as a tertiary amines such as N,N-dimethyl aminobenzoic acid ethyl ester, N,N-dimethylamino benzoic acid isoamyl ester, pentyl-4-dimethylaminobenzoate, triethylamine and triethanolamine can be added.

Examples of the commercially available photopolymerization initiator include Irgacure 261, 184, 369, 651, 500, 819, 907, 784, 2959, Darocur 1116, 1173, CGI1700, CGI1750, CGI1850, CG-24-61, Lucirin TPO, CGI-784 (product names; manufactured by BASF Japan Ltd.), DAICATII (product names; manufactured by Daicel Chemical Industries Corporation), UVAC1591 (product names; manufactured by Daisel UCB company), Rhodsil photoinitiator 2074 (product names; manufactured by Rhodia, Inc.), Uvecryl P36 (product names; manufactured by UCB S.A.), Ezacure KIP150, KIP65LT, KIP100F, KT37, KT55, KT046, KIP75/B, and ONE (product names; manufactured by Fratelli-Lamberti).

When the photopolymerization initiator is used together, the formulation ratio of the photopolymerization initiator is preferably in a range of 0.5 to 10 parts by mass in the photosensitive resin composition of the present invention of 100 parts by mass.

A photobase generator except for formula (1) may be used by replacement of the above photopolymerization initiator or in addition to the above photopolymerization initiator together. The photobase generator is a compound capable of producing one or more base materials which may work as a catalyst for additional reaction of (meta)acrylate having an epoxy group with a thermal curing component by change of molecule structure or by the cleavage of molecule by irradiation of rays such as ultraviolet rays or visible light. Examples of the base material generated include a secondary amine and a tertiary amine.

Examples of the photobase generator which can be used together include an α-amino acetophenone compound, an oxime ester compound, and a compound having one or more substituents such as an acyl oxyimino group, a N-formulation aromatic amino group, a N-acylation aromatic amino group, a nitro benzyl carbamate group or an alkoxybenzyl carbamate group. Among them, an oxime ester compound and an α-amino acetophenone compound are preferable. As an α-amino acetophenone compound, the compound having two or more nitrogen atoms is particularly preferable. As other photobase generators, WPBG-018 (product name; 9-anthrylmethyl N, N'-diethylcarbamate, manufacture by Wako Pure Chemical Industries Ltd.), WPBG-027 (product name; (E)-1-[3-(2-hydroxyphenyl)-2-propenoyl]piperidine), WPBG-082 (product name: guanidinium 2-(3-benzoylphenyl)propionate), WPBG-140 (product name; 1-(anthraquinon-2-yl)ethylimidazolecarboxylate), etc., can also be used. An α-amino acetophenone compound has a benzoin ether bond in the molecule, which provides cleavage in the molecule by irradiation to produce a base material (amine), which works as a curing catalyst. Specifically, examples of the α-amino acetophenone include commercial compounds or solutions thereof such as (4-morpholinobenzoyl)-1-benzyl-1-dimethylamino propane (Irgacure 369, product name, manufactured by BASF Japan Ltd.) and 4-(methylthiobenzoyl)-1-methyl-1-morpholino ethane (Irgacure 907, product name, manufactured by BASF Japan Ltd.), 2-(dimethylamino)-2-[(4-methylphenyl)methyl]-1-[4-(4-morpholinyl)phenyl]-1-butanone (Irgacure 379, product name, manufactured by BASF Japan Ltd.)

As an oxime ester compound which can be used together, any oxime ester compounds can be used as long as the compound can produce a base material by irradiation. Examples of the oxime ester which may be commercially available include CGI-325, Irgacure OXE01 and Irgacure OXE02 manufactured by BASF Japan Ltd, and N-1919 and NCI-831 manufactured by ADEKA CORPORATION. Also, the compound having two oxime ester groups in the molecule can be preferably used which is described in Japanese Patent No. 4,344,400.

In addition, examples include carbazole oxime ester compounds described in JP2004-359639A, JP2005-097141A, JP2005-220097A, JP2006-160634A, JP2008-094770A, JP2008-509967T, JP2009-040762T and JP2011-80036A.

A base amplifier agent which can further generate a base by decomposition or transfer reaction due to a little amount of the base generated from the base generator can be used together. Examples of the base amplifier agent include a compound having a 9-fluorenylmethyl carbamate bond, a compound having a 1,1-dimethyl-2-cyanomethylcarbamate bond $((CN)CH_2C(CH_3)_2OC(O)NR_2)$, a compound having a para-nitrobenzylcarbamate bond, a compound having a 2,4-dichlorobenzyl carbamate bond, in addition to those, examples also include a urethane compound described in paragraphs 0010 to 0032 of JP 2000-330270A and a urethane compound described in paragraphs 0033 to 0060 of JP 2008-250111A.

The addition of a sensitizer may show advantageous effects to improve the sensitivity, namely to allow the base generator to sufficiently use the energy of active energy ray which permeates the polymer. Particularly, the effect provided by the addition of the sensitizer is large, when the polyimide precursor also has absorption in a wavelength of 360 nm or more. The examples of the compound called a sensitizer include thioxanthone, diethylthioxanthone and the derivatives thereof, a coumarin and the derivatives thereof, a ketocoumarin and the derivatives thereof, a keto-bis-coumarin and the derivative thereof, cyclopentanone and the derivative thereof, cyclohexanone and the derivative thereof, thiopyrylium salt and the derivative thereof, and thioxanthene, xanthene and the derivatives thereof. Specifically, examples of the coumarin, the ketocoumarin and the derivatives thereof include 3,3'-carbonylbiscoumalin, 3,3'-carbonylbis(5,7-dimethoxy coumarin) and 3,3'-carbonylbis(7-acetoxy-coumarin). Specifically, examples of the thioxanthone and the derivatives thereof include diethyl thioxanthone and isopropyl thioxanthone. Furthermore, examples also include benzophenone, acetophenone, phenanthrene, 2-nitrofluorene, 5-nitroacenaphthene, benzoquinone, 2-ethylanthraquinone, 2-tert-butylanthraquinone, 1,2-benz anthraquinone and 1,2-naphthoquinone. The sensitizer showing the most suitable sensitization working is selected appropriately, because the above sensitizer shows particularly advantageous effects generated by the combination with the base generators.

Various organic or inorganic compounds having a small molecule or a large molecule, for example a dye, a surfactant, a leveling agent, a plasticizer, fine particles may be formulated in order to give processing properties or various kinds of functionalities to the photosensitive resin composition of the present invention. Examples of the fine particles include organic fine particles such as polystyrene and polytetrafluoroethylene, inorganic fine particles such as colloidal silica, carbon and layered silicate, which may be porous or hollow structures. Also, a pigment, a filler and fiber, etc., are the functions or the forms thereof.

Formulation ratio of the optional components except for solvents is preferably in a range of 0.1 to 95% by mass to the whole solid content of the photosensitive resin composition. When formulation ratio is less than 0.1% by mass, the effect of the addition of the additives is difficult to appear. When formulation ratio exceeds 95% by mass, the characteristic of the resin cured product is difficult to be reflected in the final products.

The photosensitive resin composition of the present invention may be used by various coating processes and forming processes to manufacture a film or a formed body having a three-dimensional shape, etc.

When the polyimide precursor and the polybenzoxazole precursor are used as a polymer precursor as an embodiment of the photosensitive resin composition of the present invention, a 5% weight reduction temperature which is obtained by the measurement of the polyimide or the polybenzoxazole in a nitrogen atmosphere is preferably 250° C. or more, more preferably 300° C. or more in view of securing the heat resistance, the dimensional stability, and the insulation. particularly, in the use for applications such as electronic components subjected to a solder reflow step, when the 5% weight reduction temperature is 300° C. or less, failure such as bubbles due to the decomposition gas generated in the solder reflow step is possible to occur.

In view of the heat resistance, the higher the glass transition temperature of the polyimide and the polybenzoxazole obtained from the photosensitive resin composition of the present invention is, the more preferable it is. In the applications including a heat forming process such as the formation of light waveguide, the glass transition temperature is preferably about 120 to 450° C., more preferably, the glass transition temperature is about 200 to 380° C.

The glass transition temperature in the present invention is obtained from a peak temperature of tan δ (tan δ=loss elasticity coefficient (E")/storage elasticity coefficient (E')) by using the dynamic viscoelasticity measurement, when the polyimide and the polybenzoxazole provided from a photosensitive resin composition can be made into a film shape. The dynamic viscoelasticity measurement can be conducted by a viscosity measuring device, for example, by Solid Analyzer RSAII (manufactured by Rheometric Scientific Ltd.) at a frequency of 3 Hz, and at a rising temperature rate of 5° C./min. When the polyimide and the polybenzoxazole obtained from the photosensitive resin composition cannot be formed into a film shape, the glass transition temperature is determined by identifying a temperature of the inflection point of baseline of the differential thermal analysis (DTA).

From the viewpoint of the dimensional stability of the polyimide and the polybenzoxazole film obtained from the photosensitive resin composition of the present invention, a linear thermal expansion coefficient is preferably 60 ppm or less, more preferably 40 ppm or less. In the production process for a semiconductor device, etc., when a film is formed on a silicon wafer, 20 ppm is further preferable from the viewpoint of adhesion and warpage of substrate.

In the present invention, the value of the linear thermal expansion coefficient of the film of the polyimide and the polybenzoxazole in the present invention can be obtained by using a thermomechanical analyzer device (TMA). The linear thermal expansion coefficient can be obtained by using a thermomechanical analyzer (for example, Thermo Plus TMA8310 manufactured by Rigaku corporation) at a rising temperature rate of 10° C./min and at a tensile loading of 1 g/25,000 μm' so that the loading per a cross-sectional area of an assessment sample can be the same.

As described above, because according to the present invention, the photosensitive resin composition can be obtained by an easy method including only mixing the photopolymerization initiator containing the compound represented by formula (1) with the polymer precursor, the composition is excellent in cost performance. Because an aromatic component containing a carboxylic acid and a basic material constituting the photopolymerization initiator containing the compound represented by formula (1) is available inexpensively, the price of the photosensitive resin composition can be suppressed. The photopolymerization initiator containing a compound represented by formula (1) may be used for reaction acceleration from various polymer precursor to the final products, and the structure of the polymer which is finally obtained can be widely selected. Furthermore, by catalytic effects of the base material of the amines generated by irradiation of the active energy ray, the treatment temperature needed for the reactions such as cyclization such as imidization for the final product from, for examples, the polyimide precursor and the polybenzoxazole precursor can decrease to reduce the load for process and the thermal damage of the products. Moreover, the base generator in the present invention generates base by irradiation of the active energy ray and heating, when the steps for producing the final product from the polymer precursor include a heating step, the base generator of the present invention uses the heating step to reduce the amount of the irradiation of the active energy ray, that is, the steps can be economically used.

The photosensitive resin composition of the present invention is suitably used for all of known fields and products using a printing ink, a paint, a sealant, an adhesive, an electronic material, a light circuit component, a forming material, a resist material, a construction material, a photoforming product, an optical component, and a resin material. The photosensitive resin composition can be used not only for the applications needed for entire exposure such as a paint, a sealant and an adhesive, but also for the applications needed for pattern forming such as a permanent film and a peeling film.

The photosensitive resin composition of the present invention is suitably used for the wide fields and the products required for the heat resistance, the dimensional stability and the insulation, for example, a paint, a printing ink, a sealant, an adhesive or a display device, a semiconductor device, an electronic part, a microelectro mechanical system (Micro Electro Mechanical System (MEMS)), a photoforming product, an optical component or a construction material. Specifically, in electronic parts, the photosensitive resin composition may be used for a printed circuit board, an interlayer insulation film and a circuit coating film as a sealing material or a layer forming material. In display devices, the photosensitive resin composition may be used for a color filter, a flexible display film, a resist material and an alignment film as a layer forming material and an image forming material. In semiconductor devices, the photosensitive resin composition may be used as a resist material and a forming material for a buffer coating film. In optical devices, the photosensitive resin composition may be used for a hologram, an optical waveguide, an optical circuit, an optical circuit component and an anti-reflection coat as an optical material and a layer forming material. In construction materials, the photosensitive resin composition may be used as a painting material and a coating material. Also, the photosensitive resin composition may be used as a material for photo fabrication. By using the photosensitive resin composition, any of a printed product, a paint, a sealant, an adhesive, a display device, a semiconductor device, an electronic part, a microelectronic mechanical system, a photo fabrication product, an optical component or a construction material may be provided.

Because the photosensitive resin composition of the present invention has features as described above, the photosensitive resin composition can be used as a pattern forming material. Particularly, when the photosensitive resin composition containing a polyimide precursor or a polybenzoxazole precursor is used as a pattern forming material (resist), the pattern formed by using the composition works as a permanent film of the polyimide or the polybenzoxazole, which is a component for providing the heat resistance and the insulation. It is suitable for the formation of a color filter, a film for flexible display, an electronic part, a semiconductor device, an interlayer insulating film, a wiring coating film, a light circuit, a light circuit component, an anti-reflection coat, other optical components or electronic members.

<Patterning Method>

The pattern forming method of the present invention is characterized by forming a coat or a formed body of the photosensitive resin compositions of the present invention, irradiating an activity energy ray to the coat or the formed body in a predetermined pattern form, and heating after the irradiation or at the same time of irradiation so as to change the solubility of the irradiated area, followed by development.

The photosensitive resin composition of the present invention is applied on a substrate to make a coat or is made into a formed body using a suitable forming method. Then, the coat or the formed body is irradiated with the active energy ray, and heated after the irradiation or at the same time of the irradiation so as to produce a radical and a base due to the opening of the photopolymerization initiator containing the compound represented by formula (1). The base material works as a catalyst for acceleration for the molecular weight increase reaction of the polymer precursor in the exposure area.

When the polymer precursor reducing the curing temperature by catalytic effect, such as a polyimide precursor or a polybenzoxazole precursor, is used, the area where a pattern is to be kept of the coat or the formed body of the photosensitive resin composition obtained by combining this polymer precursor with the photopolymerization initiator including the compound represented by formula (1) is exposed, firstly. The base material generated by irradiation or by heating at the same time of the irradiation selectively reduces the heat curing temperature of the exposed area. After the exposure or at the same time of the exposure, the coat is heated at a temperature at which the exposed area can be cured but the unexposed area cannot be cured. The heat treatment for generating a base material and the heat treatment for curing only the exposed area (bake after exposure) may be made into the same step or the different steps. Next, by dissolving the unexposed are with the predetermined developer such as organic solvents and basic aqueous solutions, the pattern of thermal-cured product is formed. The pattern is subjected to optional heat treatment to complete the thermal curing, if necessary. By the steps mentioned above, the predetermined two-dimensional resin pattern (general planar pattern) or the three-dimensional resin pattern (sterically formed shape) which is a usual negative type can be obtained.

Also, when a polymer precursor such as a compound or a polymer having an epoxy group and a cyanate group which starts the reaction by catalytic effects of the base is used, the area where a pattern is to be kept of the coat or the formed body of the photosensitive resin composition obtained by combining this polymer precursor with the photopolymerization initiator including the compound represented by formula (1) is exposed, firstly. By a radical and a basic material generated by the exposure or by heating at the same time of the exposure, the molecular weight increasing reaction of the compound having an acryloyl group, an epoxy group or a cyanate group occurs to cure only the exposed area. The heat treatment for generating a base material and the heat treatment for curing only the exposed area (bake after exposure) may be made into the same step or the different steps. Next, by dissolving the unexposed are with the predetermined developer such as organic solvents and basic aqueous solutions, the pattern of thermal-cured product is formed. The pattern is subjected to optional heat treatment to complete the thermal curing, if necessary. By the steps mentioned above, the predetermined two-dimensional resin pattern (general planar pattern) or the three-dimensional resin pattern (sterically formed shape) which is a usual negative type can be obtained.

A coat (dry firm) which does not have stickiness on the surface of the substrate can be formed by dissolving the photosensitive resin composition in a polar solvent such as propylene glycol monomethyl ether, methylethyl ketone, cyclopentanone, cyclohexanone, ethylacetate, propylene glycol monomethyl ether acetate, N,N-dimethylacetamide, N-methyl-2-pyrrolidone and γ-butyrolactone; aromatic hydrocarbons such as toluene; a mixing solvent containing the above solvents, subsequently, applying the solution containing the photosensitive resin on a substrate such as a silicon wafer, a metal substrate, a ceramic substrate and a resin film by an immersion method, a spray method, a flex printing method, a gravure printing method, a screen printing method, a spin coating method and a dispense method, and removing the solvent mostly by heating. The thickness of the coating film is not particularly limited, but the thickness is preferably 0.5 to 50 μm. In view of the sensitivity and developing speed, 1.0 to 20 μm is more preferably. The solvent is dried for removing under conditions, for examples, for 1 to 20 minutes at 80 to 100° C.

An active energy ray is irradiated to the coat through a mask having a predetermined pattern to conduct an exposure in the pattern. After the heating, the unexposed area of the coat is removed by using a suitable developer to form a cured film having a predetermined pattern.

An exposure method and an exposure device used for the exposure step are not limited, and the contact exposure and the indirect exposure can be performed. A contact/proximity exposure apparatus using a g-ray stepper, an i-ray stepper and a super high-pressure mercury vapor lamp, a mirror projection exposure apparatus or other projector and light source capable of irradiating ultraviolet rays, a visible ray, an X-ray, and an electron ray can be used.

The heating temperature for generating a base by removing a protection group by heating before, after or at the same time of exposure is appropriately selected according to the polymer precursor for combination or purpose. At the temperature of the circumstance of the place where the photosensitive resin composition is arranged (for example, a room temperature) the base is gradually generated, therefore the heating is not necessarily conducted in the case that the photosensitive resin composition is used for the purpose not requiring for quick curing, etc. The base may be also generated by the heat induced by the irradiation of the active energy ray. The higher the heating temperature is, the more efficiently the base is generated. Therefore, the heating temperature is preferably 30° C. or more, more preferably 60° C. or more, further preferably 100° C. or more, particularly preferably 120° C. or more. However, a polymer precursor may also be cured in the unexposed area at 60° C. or more, the suitable temperature is not limited to the above. For example, in the case of epoxy resin, the temperature is appropriately selected, but preferable temperature of heating treatment is usually 100 to 150° C.

When a protection group may be removed by heating before the exposure, the heating may be conducted in the heating step when the coat is dried or in other heating step. In this case, the heating temperature may be appropriately selected, as long as a protection group may be removed. The heating temperature is preferably 50 to 180° C., and the heating time is preferably 10 seconds to 60 minutes.

In order to physically accelerate a cross-linking reaction, and to react to cure the exposed area only, the post exposure bake (PEB) of the coat of the photosensitive resin composition may be preferably conducted between the exposure step and the development step. The PEB is preferably conducted at a temperature where the reaction rates of the curing reactions of imidization, etc. are different in the unexposed area where no basic compound is generated and in the exposed area where the basic compound is generated due to the irradiation of the active energy ray. For example, in the imidization, the preferable temperature of heating treatment is usually around 60 to 200° C., the more preferably 120 to 200° C. When the heating treatment temperature is less than 60° C., imidization effects are poor, and therefore, it is difficult to make the difference of imidization rates in the exposed area and in the unexposed area under the practical process conditions. When the heating treatment temperature is exceeds 200° C., the imidization in the unexposed area containing no amine may also proceed, resulting in hardly making difference of solubility of the exposed area and the unexposed area. The heat treatment is conducted by any conventional methods such as methods using a circulation oven and a hot plate in the atmosphere of air or nitrogen atmosphere, but the heat treatment is not limited to these. The photopolymerization initiator containing the compound represented by formula (1) generates a radical and a base by irradiation of the active energy ray and heating. This heat treatment for generating the basic compound and the PEB treatment are made in the same step or different steps.

(Developer)

The developer used for the developing step is not limited as long as a solution or a solvent which can dissolve the unexposed parts selectively. The developer can be appropriately selected from basic solutions and organic solvents, etc., according to the polymer precursor contained in the photosensitive resin composition of the present invention.

The basic aqueous solution as a developer is not particularly limited. Examples of the basic aqueous solution include a tetramethylammonium hydroxide (TMAH) aqueous solution having a concentration of 0.01 to 10% by mass, preferably 0.05 to 5% by mass, furthermore, a solution having a solute such as diethanolamine, diethylaminoethanol, sodium hydroxide, potassium hydroxide, sodium carbonate, potassium carbonate, sodium hydrogen carbonate, potassium hydrogen carbonate, triethylamine, diethylamine, methylamine, dimethylamine, acetic acid dimethyl aminoethyl, dimethyl aminoethanol, dimethylaminoethyl methacrylate, cyclohexylamine, ethylenediamine, hexamethylene diamine and tetramethyl ammonium.

These solutes may be used alone, or in mixture of two or more. The developer may contain an organic solvent, etc., as far as the content of water in the developer is 50% or more, preferably 70% or more.

The organic solvent as a developer is not limited. As an organic solvent, polar solvents such as N-methyl-2-pyrrolidone, N,N-dimethylformamide, N,N-dimethyl acetamide, dimethyl sulfoxide, γ-butyrolactone and dimethyl acrylamide; alcohols such as methanol, ethanol and isopropanol; esters such as ethylacetate and propylene glycol monomethyl ether acetate; ketones such as cyclopentanone, cyclohexanone, isobutyl ketone and methyl isobutyl ketone; tetrahydrofuran; chloroform; or acetonitrile may be used alone or in mixture of two.

After the development, washing is conducted with water or a poor solvent. In this case, alcohols such as ethanol and isopropyl alcohol, or esters such as ethyl lactate and propylene glycol monomethyl ether acetate may be added to the water.

After the washing, dry is performed at 80 to 100° C. to stabilize the pattern. In order to make this relief pattern have heat resistance, heating is performed at a temperature of 180 to 500° C., preferably 200 to 350° C. for from several tens of minutes to several hours to form a high heat resistance resin layer having the pattern.

EXAMPLES

The present invention now will be described in more detail with reference to Examples, but these Examples are only for the purpose of suitably illustrating the present invention and are not intended to limit the present invention by any means. Parts in Synthesis Examples and Examples represent parts by mass.

Example 1 Synthesis of Compound Represented by Formula (1) of the Present Invention (Step 1) Synthesis of Intermediate Compound Represented by Formula (31)

After 1.9 parts of potassium cyanide was dissolved by addition of 10 parts of water and 53 parts of ethanol, the solution was sonicated under nitrogen atmosphere to degas the reaction liquid. To this solution, 10 parts of 4-(methylthio) benzaldehyde represented by the following formula (30) was added dropwise, and the mixture was heated at 80° C. to start the reaction. After stirred for 30 minutes, the reaction liquid was cooled to 3° C., and precipitated crystals were collected by suction filtration. The collected solid was purified by recrystallization using a large amount of ethanol to obtain 7.6 parts of the intermediate compound represented by following formula (31).

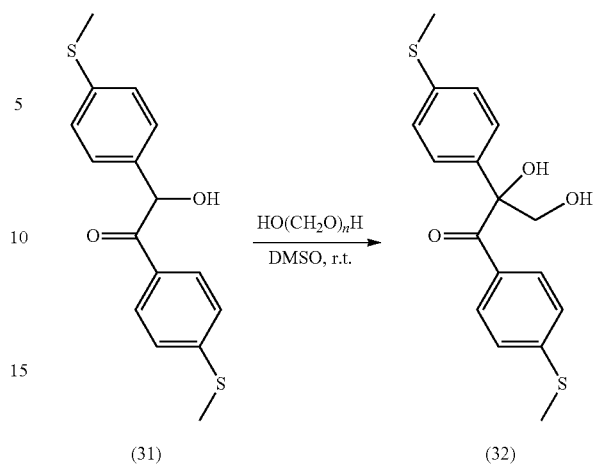

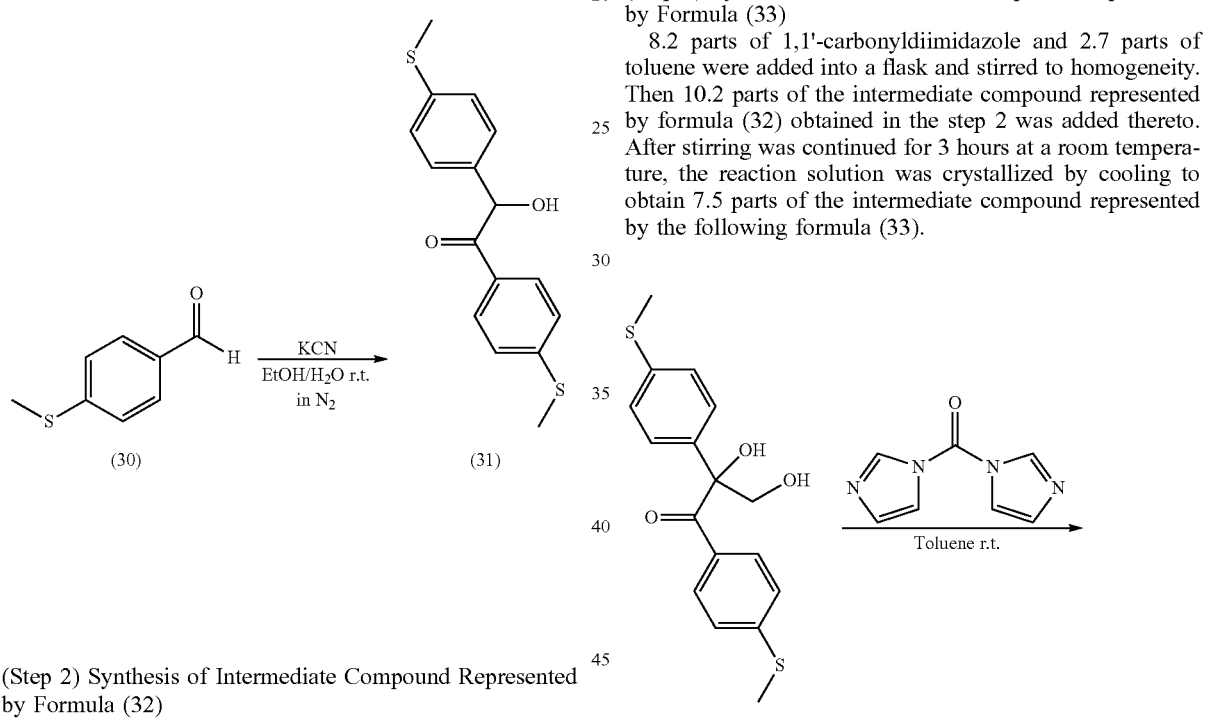

(Step 2) Synthesis of Intermediate Compound Represented by Formula (32)

To a flask equipped with a stirrer, a reflux condenser, and a stirring device, 9.0 parts of paraformaldehyde and 170 parts of dimethyl sulfoxide were added and stirred. Then a solution where 1.4 parts of potassium hydroxide was dissolved in 5 parts of ethanol was added dropwise to the flask, and the mixture was stirred until paraformaldehyde completely dissolved. A solution of 50 parts of the intermediate compound represented by formula (31) obtained in the step 1 dissolved in 30 parts of dimethyl sulfoxide was added dropwise to the dimethyl sulfoxide solution obtained above over 30 minutes, and the mixture was stirred at room temperature for 2 hours. Thereafter, 2.6 parts of 35% hydrochloric acid was added dropwise thereto for neutralization to terminate the reaction. After toluene and saturated saline were added to this reaction solution to perform extraction of the reaction product into the organic layer, the separated and concentrated organic layer was crystallized to obtain 40 parts of the intermediate compound represented by the following formula (32).

(Step 3) Synthesis of Intermediate Compound Represented by Formula (33)

8.2 parts of 1,1'-carbonyldiimidazole and 2.7 parts of toluene were added into a flask and stirred to homogeneity. Then 10.2 parts of the intermediate compound represented by formula (32) obtained in the step 2 was added thereto. After stirring was continued for 3 hours at a room temperature, the reaction solution was crystallized by cooling to obtain 7.5 parts of the intermediate compound represented by the following formula (33).

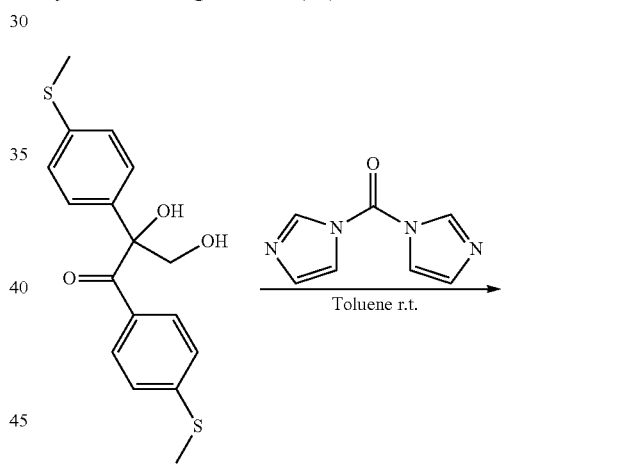

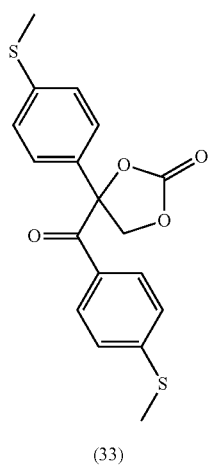

(Step 4) Synthesis of Compound of the Present Invention Represented by Following Formula (C-1) (Phopolymerization Initiator C-1)

0.08 parts of 1,5,7-triazabicyclo [4,4,0]deca-5-ene, 1.0 parts of piperidine and 28 parts of toluene were added into a flask and stirred to homogeneity. Then, 2.0 parts of the intermediate compound represented by formula (33) obtained in the step 2 was added thereto. After stirring was continued for 3 hours at a mixture temperature of 60° C., the reaction solution was crystallized by cooling to obtain 1.3 parts of the compound of the present invention represented by the following formula (C-1) (initiator C-1).

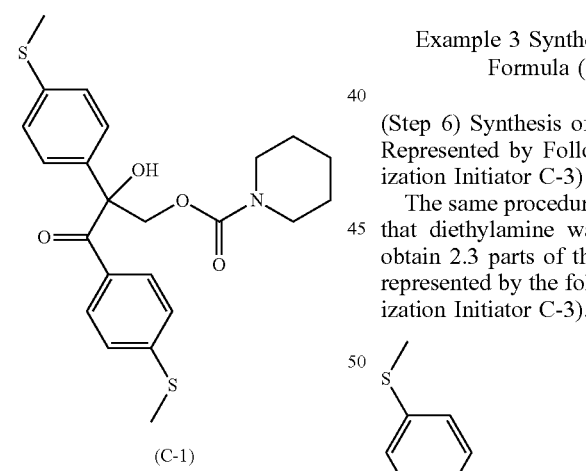

(33)

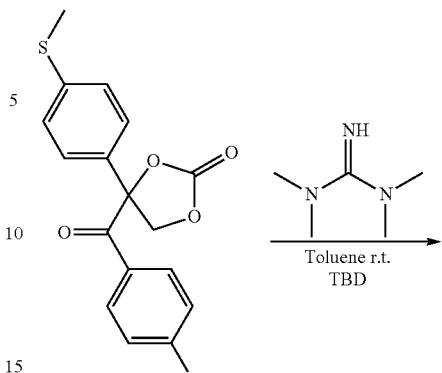

(33)

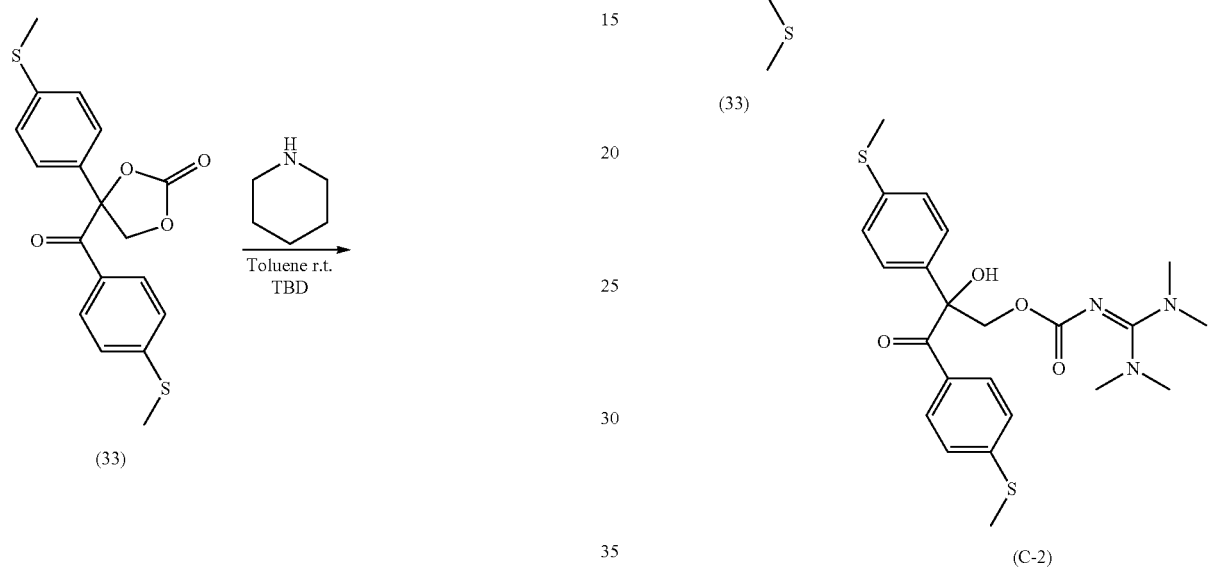

(C-2)

Example 2 Synthesis of Compound Represented by Formula (1) of the Present Invention (Step 5) Synthesis of Compound of the Present Invention Represented by Following Formula (C-2) (Photopolymerization Initiator C-2)

The same procedure as in the step 4 was repeated, except that 1,1,3,3-tetramethylguanidine was used instead of the piperidine to obtain 1.5 parts of the compound of the present invention represented by the following formula (C-2) (Photopolymerization Initiator C-2).

Example 3 Synthesis of Compound Represented by Formula (1) of the Present Invention (Step 6) Synthesis of Compound of the Present Invention Represented by Following Formula (C-3) (Photopolymerization Initiator C-3)

The same procedure as in the step 4 was repeated, except that diethylamine was used instead of the piperidine to obtain 2.3 parts of the compound of the present invention represented by the following formula (C-3) (photopolymerization Initiator C-3).

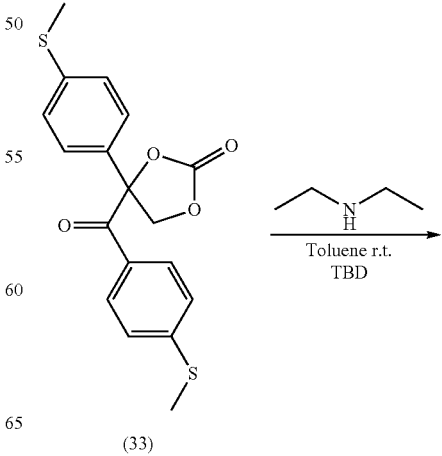

(33)

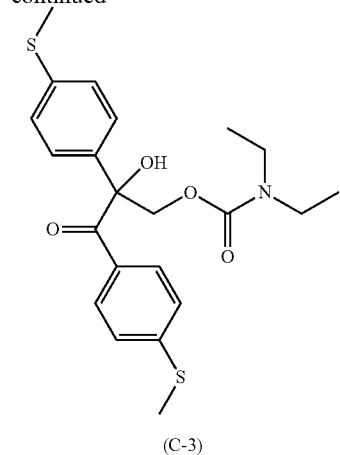

(C-3)

Example 4 Synthesis of Compound Represented by Formula (1) of the Present Invention (Step 7) Synthesis of Compound of the Present Invention Represented by Following Formula (C-4) (Photopolymerization Initiator C-4)

The same procedure as in the step 4 was repeated except that 2-aminopyridine was used instead of the piperidine to obtain 1.1 parts of the compound of the present invention represented by the following formula (C-4) (Photopolymerization Initiator C-4).

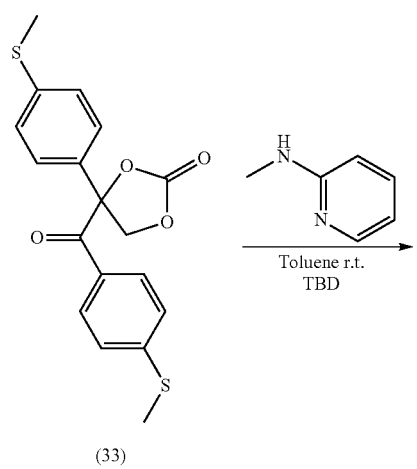

(33)

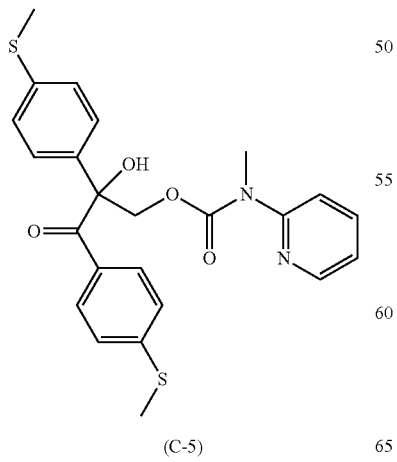

(C-5)

Example 5 Synthesis of Compound Represented by Formula (1) of the Present Invention (Step 8) Synthesis of Compound of the Present Invention Represented by Following Formula (C-5) (Photopolymerization Initiator C-5)

The same procedure as in the step 4 was repeated, except that 2-methylaminopyridine was used instead of the piperidine to obtain 1.6 parts of the compound of the present invention represented by the following formula (C-5) (Photopolymerization Initiator C-5).

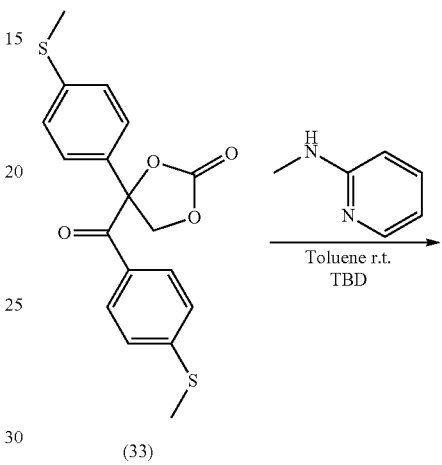

(33)

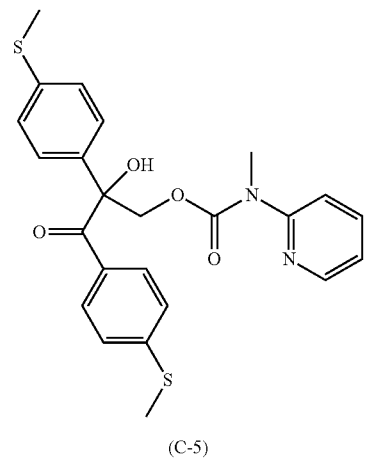

(C-5)

Example 6 Synthesis of Compound Represented by Formula (1) of the Present Invention (Step 9) Synthesis of Compound of the Present Invention Represented by Following Formula (C-6) (Photopolymerization Initiator C-6)

The same procedure as in the step 4 was repeated, except that 2-amino-5-cyanopyridine was used instead of the piperidine to obtain 1.6 parts of the compound of the present invention represented by the following formula (C-6) (Photopolymerization Initiator C-6).

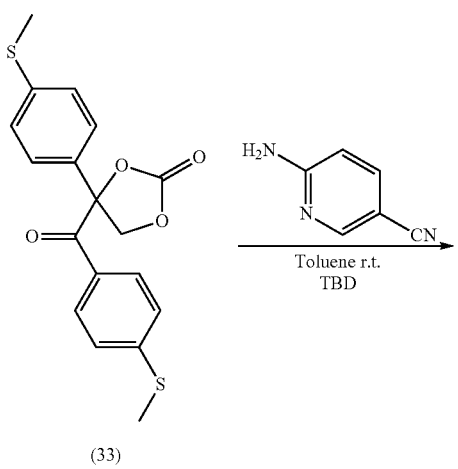

(33)

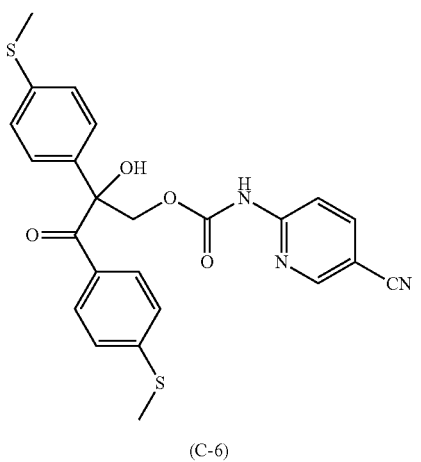

(C-6)

Examples 7 to 12 and Comparative Examples 1 to 3 Preparation of Photosensitive Resin Composition Respective components were mixed in accordance with the amounts (parts by mass) to be blended listed in Table 1 to obtain photosensitive resin compositions.

(Formation and Heat Treatment of the Coat Made from the Photosensitive Resin Composition)

Each of the photosensitive resin composition of Examples 7 to 12 and Comparative Examples 1 to 3 was coated onto a double-sided easy adhesion PET film having a film thickness of 100 μm (COSMOSHINE A4300 manufactured by TOYOBO Co., LTD.) with #14 bar coater. Then heat treatment (bake before exposure) was conducted at 80° C. for 1 minute using an oven to remove a solvent.

(Exposure Treatment and Heat Treatment)

The coat obtained above on the PET film was subjected to three-pass exposure using a belt conveyor-type exposure machine mercury lamp under the conditions that exposure amount of 1 pass is 100 mJ/cm$^2$ (the distance from belt conveyor to high-pressure mercury lamp is 100 mm.). After that heat treatment (bake after exposure) was conducted at 60° C. for 15 minutes using an oven to obtain the cured product of each photosensitive resin composition (cured film having a film thickness of 10 μm).

For the cured product of each photosensitive resin composition, the following evaluations were conducted. The results are shown in Table 1.

(1) Pencil Hardness:

Pencil hardness was measured by the method according to JIS K-5600 with a weight load of 750 g.

(2) Scratch Resistance:

After rubbing with #0000 steal wool with a weight load of 1000 g and 20 times, the conditions of the surface were visually observed and evaluated by the following evaluation criteria.

○: There is no scratch.
Δ: There are scratches slightly.
X: There are scratches obviously.

TABLE 1

Evaluation results of the photosensitive resin compound

| | | Example | | | | | | Comparative Example | | |
|---|---|---|---|---|---|---|---|---|---|---|
| | | 7 | 8 | 9 | 10 | 11 | 12 | 1 | 2 | 3 |
| Iinitiator | C-1 | 0.015 | 0 | 0 | 0 | 0 | 0 | 0 | 0 | 0 |
| | C-2 | 0 | 0.015 | 0 | 0 | 0 | 0 | 0 | 0 | 0 |
| | C-3 | 0 | 0 | 0.015 | 0 | 0 | 0 | 0 | 0 | 0 |
| | C-4 | 0 | 0 | 0 | 0.015 | 0 | 0 | 0 | 0 | 0 |
| | C-5 | 0 | 0 | 0 | 0 | 0.015 | 0 | 0 | 0 | 0 |
| | C-6 | 0 | 0 | 0 | 0 | 0 | 0.015 | 0 | 0 | 0 |
| | C-7 | 0 | 0 | 0 | 0 | 0 | 0 | 0.015 | 0 | 0 |
| | C-8 | 0 | 0 | 0 | 0 | 0 | 0 | 0 | 0.015 | 0 |
| | C-9 | 0 | 0 | 0 | 0 | 0 | 0 | 0 | 0 | 0.015 |
| DPHA | | | | | 0.3 | | | | | |
| KBM-5103 | | | | | 0.075 | | | | | |
| TEOS | | | | | 0.3 | | | | | |
| MEK | | | | | 0.04 | | | | | |

TABLE 1-continued

Evaluation results of the photosensitive resin compound

| | Example | | | | | | Comparative Example | | |
|---|---|---|---|---|---|---|---|---|---|
| | 7 | 8 | 9 | 10 | 11 | 12 | 1 | 2 | 3 |
| Pencil hardness | 4H | 4H | 3H | 4H | 3H | 3H | H | 2H | uncured |
| Scratch resistance | ○ | ○ | ○ | ○ | ○ | ○ | X | Δ | — |

(C-1): The compound represented by formula (A-1) obtained in Example 1
(C-2): The compound represented by formula (A-2) obtained in Example 2
(C-3): The compound represented by formula (A-3) obtained in Example 3
(C-4): The compound represented by formula (A-4) obtained in Example 4
(C-5): The compound represented by formula (A-5) obtained in Example 5
(C-6): The compound represented by formula (A-6) obtained in Example 6
(C-7): The compound described in Patent Literature 5 (Irg. 369 manufactured by BASF Ltd.)
(C-8): The compound synthsized by the method described in the steps 9 through 11 in Example 6 in Patent Literature 6
(C-9): The compound (PBG1) systhsized by the method described in Non Patent Literature 1
(DPHA): dipentaerythritolhexaacrylate
(KBM-5103): silane coupling agent manufactured by Shin-Etsu Chemical Co., Ltd.
(TEOS): o-tetraethylsilicate
(MEK): methyethyketone When irradiation was conducted under the same conditions, the photosensitive resin compositions of the Examples had excellent pencil hardness and excellent scratch resistance. Therefore, it was found that the curing reactions of the photosensitive resin compositions of the Examples proceeded in high efficiency even by the irradiation of the light with a wavelength of high-pressure mercury lamp.

INDUSTRIAL APPLICABILITY

The photo polymerization initiator of the present invention generates the base having high base strength and the curing reaction of the photosensitive resin composition containing the photo polymerization initiator proceeds in high efficiency by the irradiation of the active energy ray with a long wavelength. In addition, there is no concern about the corrosion of metal substrate by the irradiation. In conclusion, the photosensitive resin composition of the present invention is useful.

The invention claimed is:

1. A compound having a following chemical formula (1):

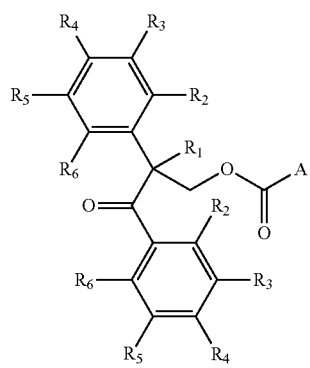
(1)

wherein in formula (1), $R_1$ represents a hydroxy group, an alkoxy group or an organic group other than the aforementioned substituents; $R_2$, $R_3$, $R_5$ and $R_6$ each independently represent hydrogen atom, halogen atom, hydroxy group, alkoxy group, mercapto group, sulfide group, silyl group, silanol group, nitro group, nitroso group, cyano group, sulfino group, sulfo group, sulfonato group, phosphino group, phosphinyl group, phosphono group, phosphonato group, amino group, ammonio group or an organic group other than the aforementioned substituents, each of $R_2$, $R_3$, $R_5$ and $R_6$ plurally existing may be the same or different from each other; $R_2$ and $R_3$ on the same benzene ring may be connected to form a ring structure and $R_5$ and $R_6$ on the same benzene ring may be connected to form a ring structure; $R_4$ each independently represents a hydrogen atom or an organic group having a thioether bond, and at least one of $R_4$ is the organic group having a thioether bond; the organic group having a thioether bond represented by $R_4$ and $R_3$ or $R_5$ may be connected to form a ring structure; A is a substituent having a formula (1-1) or (1-2):

(1-1)

(1-2)

wherein in formula (1-1), $R_7$ and $R_8$ each independently represent a hydrogen atom or an alkyl group or a hetero cyclic group, or $R_7$ and $R_8$ may be connected to form a cyclic group; in formula (1-2), $R_9$ and $R_{10}$ each independently represent an amino group or a substituted amino group.

2. The compound according to claim 1, wherein one of $R_4$ is an alkyl group having a thioether bond or an aryl group having a thioether bond, and the other is the hydrogen atom, an alkyl group having a thioether bond or an aryl group having a thioether bond.

3. The compound according to claim 1, wherein $R_1$ is the hydroxy group.

4. A photopolymerization initiator containing the compound according to claim 1.

5. A photosensitive resin composition containing the photopolymerization initiator according to claim 4 and a polymer precursor capable of being polymerized by irradiation or by both of irradiation and heating in presence of a photopolymerization initiator.

6. The photosensitive resin composition according to claim 5, wherein the polymer precursor comprises at least one selected from the group consisting of a compound having a substituent selected from the group consisting of an epoxy group, an isocyanate group, an oxetane group, an acryloyl group, a methacryloyl group, a maleimide group and a thiirane group; a polysiloxane precursor; a polyimide precursor; and a polybenzoxazole precursor.

7. The photosensitive resin composition according to claim 6, wherein the polymer precursor comprises the compound having an epoxy group.

8. The photosensitive resin composition according to claim 6, wherein the polymer precursor comprises the compound having an acryloyl group and the polysiloxane precursor.

9. A cured product comprising the photosensitive resin composition according to claim 5.

* * * * *